US008710193B2

(12) United States Patent
Irie et al.

(10) Patent No.: US 8,710,193 B2
(45) Date of Patent: Apr. 29, 2014

(54) ANTIBODY RECOGNIZING TURN STRUCTURE IN AMYLOID β

(75) Inventors: Kazuhiro Irie, Kyoto (JP); Kazuma Murakami, Kyoto (JP); Yuichi Masuda, Kyoto (JP); Takahiko Shimizu, Tokyo (JP); Takuji Shirasawa, Tokyo (JP); Tsutomu Seito, Fujioka (JP)

(73) Assignees: Kyoto University, Kyoto (JP); Tokyo Metropolitan Geriatric Hospital and Institute of Gerontology, Tokyo (JP); Immuno-Biological Laboratories Co., Ltd., Gunma (JP)

( * ) Notice: Subject to any disclaimer, the term of this patent is extended or adjusted under 35 U.S.C. 154(b) by 0 days.

(21) Appl. No.: 13/502,347

(22) PCT Filed: Oct. 18, 2010

(86) PCT No.: PCT/JP2010/006162
§ 371 (c)(1),
(2), (4) Date: Apr. 16, 2012

(87) PCT Pub. No.: WO2011/045945
PCT Pub. Date: Apr. 21, 2011

(65) Prior Publication Data
US 2012/0219552 A1    Aug. 30, 2012

(30) Foreign Application Priority Data
Oct. 16, 2009   (JP) ................ 2009-239542

(51) Int. Cl.
C07K 16/18   (2006.01)
C07K 16/46   (2006.01)
A61B 5/145   (2006.01)
A61K 39/395  (2006.01)

(52) U.S. Cl.
USPC ......... 530/388.85; 435/7.1; 435/7.6; 435/7.7; 424/9.1; 424/139.1

(58) Field of Classification Search
None
See application file for complete search history.

(56) References Cited

FOREIGN PATENT DOCUMENTS

JP    2006-265189    10/2006

OTHER PUBLICATIONS

Wang et al., Acta Biochim Biophys Sin, 44:807-814, Aug. 2012.*
Fawzi et al., Biophysical Journal, 94:2007-2016, Mar. 2008.*
Masuda et al., "Identification of Physiological and Toxic Conformations in Aβ42 Aggregates," ChemBioChem (2009) 10:287-295.
Muakami et al., "Formation and Stabilization Model of the 42-mer Aβ Radical: Implications for the Long-Lasting Oxidative Stress in Alzheimer's Disease," J. Am. Chem. Soc. (2005) 127(43):15168-15174.
Murakami et al., "Monoclonal Antibody Against the Turn of the 42-Residue Amyloid β-Protein at Positions 22 and 23," ACS Chem. Neuroscience (2010) DOI: 10. 1021/cn100072e.
Shimizu et al., "Biological Significance of Isoaspartate and Its Repair System," Biol. Pharm. Bull. (2005) 28(9):1590-1596.
Morimoto et al., "Aggregation and Neurotoxicity of Mutant Amyloid β (A β) Peptides with Proline Replacement: Importance of Turn Formation at Positions 22 and 23," Biochemical and Biophysical Research Communications (2002) 295:306-311.
Corrected Search Opinion for European Patent Application No. 10823213.3 issued May 27, 2013.
Office Action (including translation) for CN 201080046483.9, mailed Jul. 15, 2013, 8 pages.

* cited by examiner

*Primary Examiner* — Daniel E Kolker
*Assistant Examiner* — Stacey N MacFarlane
(74) *Attorney, Agent, or Firm* — Morrison & Foerster LLP

(57) ABSTRACT

Provided is a therapeutic method exclusively targeting an amyloid β protein (Aβ) having a specific turn structure of Aβ. Specifically provided is an antibody which specifically recognizes an amyloid β having a turn structure at amino acids positions 22 and 23. Also provided are a medicinal composition comprising, as the active ingredient, an antibody specifically recognizing a toxic conformer of amyloid β, an assay kit for a toxic conformer of amyloid β, a diagnostic for Alzheimer's disease, etc.

12 Claims, 5 Drawing Sheets

SEQUENCE LISTING

```
<160> NUMBER OF SEQ ID NOS: 1

<210> SEQ ID NO 1
<211> LENGTH: 27
<212> TYPE: PRT
<213> ORGANISM: Artificial
<220> FEATURE:
<223> OTHER INFORMATION: Immunogen peptide

<400> SEQUENCE: 1
```

```
Cys Tyr Glu Val His His Gln Lys Leu Val Phe Phe Ala Pro Asp Val
1               5                   10                  15

Gly Ser Asn Lys Gly Ala Ile Ile Gly Leu Met
            20                  25
```

ANTIBODY RECOGNIZING TURN STRUCTURE IN AMYLOID β

CROSS-REFERENCE TO RELATED APPLICATIONS

This application is the national phase of PCT application PCT/JP2010/006162 having an international filing date of 18 Oct. 2010, which claims benefit of Japanese application No. 2009-239542 2009 filed 16 Oct. 2009. The contents of the above patent applications are incorporated by reference herein in their entirety.

REFERENCE TO SEQUENCE LISTING FILED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 643102001500seqlist.txt | Apr. 13, 2012 | 4,096 |

TECHNICAL FIELD

The present invention relates to a method for measuring amyloid β having a turn structure at amino acids positions 22 and 23, and a method for the diagnosis of and a method for a treatment of Alzheimer's disease.

BACKGROUND ART

Alzheimer's disease (hereinafter, referred to as "AD") is generally characterized by accumulation of amyloid in a senile plaque. Amyloid is mainly amyloid ρ proteins of 40 and 42 amino acid residues (hereinafter, referred to as "Aβ40" and "Aβ42", respectively). These proteins are generated by degradation of an amyloid precursor protein (APP) by two proteases, β- and γ-secretases. In the onset of AD, Aβ42 has been considered to take a more important role than Aβ40 due to its aggregation propensity and neural toxicity. Recent study has shown that an oxidation stress contributes to neurodegenaration associated with AD. Radical forming-mediated neural toxicity of Aβ42 is closely associated with radicalization of tyrosine at position 10 and at position 35 which accompanies generation of active oxygen species. In addition, there has been an evidence that accumulation of an oligomer of Aβ induces AD through synaptic toxicity.

An Alzheimer's disease model mouse inoculated with an Aβ aggregate as a vaccine showed reduced sedimentation of Aβ in a brain and inhibition of a cognitive function disorder. Therefore, immunization with Aβ had been appeared to be a promising method for AD treatment. However, a clinical trial of immunization of an AD patient with Aβ42 (AN1792) was dropped due to the severe side effect of excessive immunity activation. One of the reasons of this problem is appeared unintentional removal of physiological Aβ42. Therefore, it has been recognized as an essential feature to discriminate Toxic Aβ42 from physiological Aβ42 for effective inhibition of amyloid plaque formation and of progression of a cognitive function disorder in an AD patient.

A study using a solid NMR method and a systematic proline substitution method has revealed. A toxic conformer of Aβ42 having a turn structure at positions 22 and 23 and physiological conformer of Aβ42 having a turn structure at positions 25 and 26 (Non-Patent Document 1, Patent Document 1). It has also been reported that the former conformer exhibits the powerful aggregating ability and neural toxicity.

CITED DOCUMENTS

Patent Document

Patent Document 1: JP2006-265189A

Non-Patent Document

Non-Patent Document 1: K. Murakami et al. (2005), J. Am. Chem. Soc., 127: 15168-15174

SUMMARY OF INVENTION

The present inventors have investigated and searched for a method for effectively distinguishing a difference in a turn structure of Aβ or for targeting only Aβ having a particular turn structure. Since a toxic conformer having a turn structure at positions 22 and 23 of Aβ42 is reversibly converted into a physiological conformer having a turn structure at positions 25 and 26 of Aβ42, its steric structure is not fixed. Therefore it was difficult to raise an antibody specifically recognizing a toxic conformer having a turn structure at a positions 22 and 23 of Aβ42 using wild-type Aβ42. In order to solve this problem resulting from unstability of the structure, the present inventors tried to raise an antibody specifically recognizing a toxic conformer having a turn structure at amino acid at positions 22 and 23 of Aβ42 using an antigen in which a turn structure at position 22 is fixed, by substituting glutamic acid at position 22 with proline. Since an antibody strictly recognizes and discriminates a difference of an amino acid, use of a mutant protein with amino acid mutation incorporated into recognition sites (positions 22 and 23) of an objective antibody (Aβ42 in which an amino acid at position 22 is substituted by proline) as an antigen could hardly raise an antibody recognizing a wild-type protein (Aβ42 in which an amino acid at position 22 is glutamic acid) without mutation. Despite this, the present inventors surprisingly succeeded in isolation an antibody specifically recognizing a wild-type toxic conformer of Aβ42 with turn structure at positions 22 and 23 of amino acids sequence from antibodies raised against the mutant antigen by using an accurate and careful screening, and achieved the present invention.

The present invention is directed to an antibody specifically recognizing a toxic conformer of Aβ having a turn structure at amino acid positions 22 and 23, and use thereof. Specifically, the present invention is directed to the following inventions.

(1) An antibody specifically recognizing Aβ having a turn structure at amino acid positions 22 and 23 (hereinafter referred to as "22-23 turn Aβ").

(2) A pharmaceutical composition comprising a substance which specifically binds to 22-23 turn Aβ as an active ingredient.

(3) The pharmaceutical composition according to (2), which is a therapeutic agent for treating Alzheimer's disease.

(4) A kit for measuring 22-23 turn Aβ, including a substance which specifically binds to 22-23 turn Aβ.

(5) A diagnostic agent for Alzheimer's disease comprising a substance which specifically binds to 22-23 turn Aβ.

(6) A method for measuring level of 22-23 turn Aβ in a sample, comprising a step of contacting the sample with a substance which specifically binds to 22-23 turn Aβ.

(7) A method for diagnosing Alzheimer's disease, comprising a step of detecting 22-23 turn Aβ in a sample.

(8) A method for diagnosing Alzheimer's disease, comprising steps of:

a) a step of preparing a sample derived from a subject,
b) a step of contacting the sample with at least one antibody which specifically recognizes 22-23 turn Aβ,
c) a step of detecting binding of the antibody to 22-23 turn Aβ and measure a level of 22-23 turn Aβ, and
d) a step of correlating the level of 22-23 turn Aβ with the presence or the absence or with a severity of Alzheimer's disease in the subject.

(9) A method for measuring a ratio of 22-23 turn Aβ to entire amyloid β in a sample comprising:

a step of measuring a level of entire amyloid β in the sample,
a step of measuring a level of 22-23 turn Aβ in the sample, and
a step of calculating a ratio of the 22-23 turn Aβ level to the entire amyloid β level from measured levels.

(10) A method for diagnosing Alzheimer's disease comprising:

a step of measuring a level of entire amyloid β in the sample,
a step of measuring a level of 22-23 turn Aβ in the sample,
a step of calculating a ratio of the 22-23 turn Aβ level to the entire amyloid β level from measured levels, and
a step of correlating the ratio of the 22-23 turn Aβ level to the entire amyloid β level with the presence or the absence or with a severity of Alzheimer's disease.

As used herein, an antibody or substance "specifically binds" or "specifically recognizes" means that the antibody or the substance binds to 22-23 turn Aβ with substantially higher affinity than other amino acid sequence or steric structure. "Substantially higher affinity" means high affinity which enables the objective amino acid sequence or objective steric structure to be distinguished from other amino acid sequence or other steric structure, by using a suitable measuring apparatus or method. Substantially higher affinity can be an affinity with a binding constant ($K_a$), for example, at least $10^7 M^{-1}$, preferably at least $10^8 M^{-1}$, and more preferably at least $10^9 M^{-1}$. Further more preferably, such binding constant is greater than $10^{10} M^{-1}$, $10^{11} M^{-1}$, or $10^{12} M^{-1}$, for example, $10^{13} M^{-1}$ or more.

The present invention is directed to an antibody which specifically recognizes 22-23 turn Aβ. There is no particular limitation to the recognition site of the antibody which specifically recognizes 22-23 turn Aβ of the present invention, as long as the antibody specifically recognizes Aβ having a turn structure at amino acid positions 22 and 23. An antibody which recognizes amino acid position 22 and/or 23 of Aβ, and/or its adjacent amino acid(s) (preferably, within a few residues from amino acid position 22 and/or 23 of Aβ) is preferable. For example, the antibody of the present invention may be an antibody which specifically recognizes 22-23 turn Aβ, and which recognizes at least one of amino acids at positions 22 and 23 of Aβ. More preferably, the antibody of the present invention is an antibody which specifically recognizes a steric structure of a turn structure constructed from amino acids at positions 22 and 23 of Aβ. For example, the antibody of the present invention may be an antibody which specifically recognizes a steric structure of a turn structure constructed from amino acids at positions 22 and 23 of Aβ, and which recognizes at least one of amino acids at positions 22 and 23 of Aβ.

The 22-23 turn Aβ which is recognized by the antibody of the present invention is not limited as long as it "has a turn structure at amino acid positions 22 and 23", and is preferably 22-23 turn Aβ40 or 22-23 turn Aβ42, more preferably 22-23 turn Aβ42. The 22-23 turn Aβ which is recognized by the antibody of the present invention includes a polypeptide having a turn structure at amino acid positions 22 and 23, and having substantially the same amino acid sequence as that of wild-type Aβ. Preferably, the 22-23 turn Aβ which is recognized by the antibody of the present invention is wild-type Aβ having a turn structure at amino acid positions 22 and 23.

Herein, "a polypeptide or a protein having substantially the same amino acid sequence" as that of a particular polypeptide or protein means a polypeptide or a protein having substantially equivalent biological properties to that of said particular polypeptide or protein of 22-23 turn Aβ, and having an amino acid sequence in which a plurality of amino acids, preferably 1 to 10 amino acids, more preferably one to a few (for example, 1 to 5, 1 to 4, 1 to 3, 1 to 2) amino acids of an amino acid sequence of said particular polypeptide or protein are substituted, deleted and/or modified, and/or in which a plurality of amino acids, preferably 1 to 10 amino acids, more preferably 1 to a few (for example, 1 to 5, 1 to 4, 1 to 3, 1 to 2) amino acids are added or inserted into its amino acid sequence. The polypeptide or protein having substantially the same amino acid sequence may be a mutant polypeptide or protein having a plurality of mutations selected from said substitution, deletion, modification and addition. Preferably, "the polypeptide or protein having substantially the same amino acid sequence" has the equivalent biological activity to that of said particular polypeptide or protein.

The antibody of the present invention may be a polyclonal antibody or a monoclonal antibody, and is preferably a monoclonal antibody. In the present invention, "the monoclonal antibody" is highly specific for an antigen, and recognizes a single antigen. Further, the antibody of the present invention includes a non-human animal antibody, an antibody having both of an amino acid sequence of a non-human animal antibody and an amino acid sequence of an antibody derived from a human, and a human antibody. The non-human animal antibody includes antibodies from mouse, rat, hamster, guinea pig, rabbit, dog, monkey, sheep, goat, chicken, duck etc. Preferably, the non-human antibody is an antibody from an animal which can be used for creating a hybridoma, and more preferably is an antibody from mouse. Examples of the antibody having both of an amino acid sequence of a non-human animal antibody and an amino acid sequence of an antibody derived from a human includes human chimeric antibody, and humanized antibody. In the above, the "chimeric antibody" is a genetically modified (genetically engineered) antibody in which a constant region of a non-human animal antibody which specifically binds to 22-23 turn Aβ is modified to constant region of a human antibody. Preferably the chimeric antibody is a mouse-human chimeric antibody (see European Patent Publication EP0125023A). The "humanized antibody" is a genetically modified (genetically engineered) antibody in which a primary structure other than a complementarity recognition region (CDR) of an H chain and an L chain of an antibody derived from a non-human animal which specifically binds to 22-23 turn Aβ is to a corresponding primary structure of a human antibody. Herein, CDR can be defined by of Kabat et al. ("Sequences of Proteins of Immunological Interest", Kabat, E. et al., U.S. Department of Health and Human Services, 1983) or by Chothia et al. (Chothia & Lesk (1987), J. Mol. Biol., 196: 901-917). "Human antibody" means a human antibody as an expression product of a completely human-derived antibody gene, and for example, includes a monoclonal antibody produced by a transgenic animal in which a gene relating to production of a human antibody has been introduced (see European Patent Publication EP0546073A) etc. For example, when the antibody of the present invention is employed in treatment, prevention, or diagnosis which requires administration of the antibody to a body, the antibody of the present invention is preferably a non-human animal/human chimeric antibody, a humanized antibody, or a human antibody.

The number of amino acids to be recognized by the antibody of the present invention is not limited as long as the antibody can bind to 22-23 turn Aβ. When the antibody is employed as a therapeutic agent, the antibody preferably recognizes the number of amino acids that enables to inhabit the function of 22-23 turn Aβ. The number of amino acids to be recognized by the antibody or a fragment thereof is preferably at least 1, more preferably at least 3. An immunoglobulin class of the antibody of the present invention is not particularly limited, and may be IgG, IgM, IgA, IgE, IgD, and IgY, and is preferably IgG. The antibody of the present invention includes any isotype of antibody.

A fragment of the antibody which specifically recognizes 22-23 turn Aβ is also included in the antibody which specifically recognizes 22-23 turn Aβ of the present invention. Herein, the "fragment of an antibody" is a portion (partial fragment) of an antibody that retains effect of the antibody on an antigen. Examples of such fragment of an antibody include $F(ab')_2$, Fab', Fab, single-stranded Fv (hereinafter, referred to as "scFv"), disulfide-bound Fv (hereinafter, referred to as "dsFv") or a polymer thereof, a dimerized V region (hereinafter, referred to as "Diabody"), or a peptide including CDR. $F(ab')_2$ is an antibody fragment of a molecular weight of about 100 thousands having antigen binding activity obtained by treating IgG with a protease pepsin. Fab' is an antibody fragment of a molecular weight of about 50 thousands having antigen binding activity obtained by cleaving a disulfide bond in a hinge region of the F (ab'). sdFv is a polypeptide having antigen binding activity, in which one VH and one VL are connected with a peptide linker. dsFv is a fragment having antigen binding activity, in which an amino acid residue is substituted with a cysteine residue in VH and VL and VH and VL is bound via a disulfide bond. Diabody is a fragment in which scFv is dimerized. Diabody of the present invention may be monospecific, or bispecific (multiple specific antibody). Dimerized scFvs may be the same or different.

Further, a peptide including a part of an antibody which specifically recognizes 22-23 turn Aβ is also included in the antibody which specifically recognizes 22-23 turn Aβ of the present invention. Herein, the "peptide including a part of an antibody" is a peptide including a part of an amino acid sequence constituting an antibody, and retaining effect of the antibody on an antigen. In this specification, the "effect of the antibody on an antigen" means binding action ability of the antibody to 22-23 turn Aβ, and particularly, when the antibody which specifically recognizes 22-23 turn Aβ of the present invention is used as a therapeutic agent or a preventive agent, means effect of inhibiting neural toxicity of Aβ and/or effect of inhibiting aggregation of Aβ. The peptide including a part of an antibody may include an amino acid sequence which is not derived from the antibody. The peptide including a part of the antibody which specifically recognizes 22-23 turn Aβ is preferably a peptide including a CDR sequence of the antibody which specifically recognizes 22-23 turn Aβ. Herein, the peptide including a CDR sequence is a peptide including an amino acid sequence of at least one CDR selected from CDR1, CDR2 and CDR3 of a heavy chain variable region and CDR1, CDR2 and CDR3 of a light chain variable region. More preferably, the peptide including a part of an antibody which specifically recognizes 22-23 turn Aβ is a peptide including an amino acid sequence of CDR3 of a heavy chain variable region and/or CDR3 of a light chain variable region.

Throughout the present specification, the "antibody which specifically recognizes Aβ having a turn structure at amino acid positions 22 and 23 (22-23 turn Aβ)" is preferably an IBL-101 monoclonal antibody produced by hybridoma cell line Amyloid β Hybridoma IBL-101 (date of deposit is Oct. 14, 2009, and registration number is FERM BP-11290) which was deposited at the National Institute of Advanced Industrial Science and Technology, Incorporated Administrative Agency, International Patent Organism Depository (Tsukuba Center Central 6, 1-1-1 Higashi, Tsukuba-shi, Ibaraki, Japan). For example, the antibody of the present invention may be a polypeptide or an antibody which have substantially the same amino acid sequence as that of the IBL-101 monoclonal antibody and which retains effect of the antibody on an antigen (for example, binding ability, and when used as a therapeutic agent or a preventive agent, preferably effect of inhibiting neural toxicity of Aβ and/or effect of inhibiting aggregation of Aβ), a chimeric antibody having a variable region of the IBL-101 monoclonal antibody and a constant region of an antibody derived from a human (hereinafter, referred to as "IBL-101 chimeric antibody"), or an antibody having a complementarity recognition region (CDR) of H-chain and L-chain of the IBL-101 monoclonal antibody (hereinafter, referred to as "IBL-101 humanized antibody") (hereinafter, these antibodies are collectively named as "antibody created based on IBL-101 monoclonal antibody"). The IBL-101 humanized antibody is, for example, an antibody having CDR1 of H-chain (hereinafter, referred to as "CDRH1"), CDRH2 and/or CDRH3 of the IBL-101 monoclonal antibody, and/or CDR1 of L-chain (hereinafter, referred to as "CDRL1"), CDRL2 and/or CDRL3 of the IBL-101 monoclonal antibody, preferably an antibody having CDRH1, CDRH2 and CDRH3 of the IBL-101 monoclonal antibody, and CDRL1, CDRL2 and CDRL3 of the IBL-101 monoclonal antibody. The antibody of the present invention may be a fragment (F $(ab')_2$, Fab', Fab, scFv, dsFv or a polymer thereof, Diabody, or a peptide including CDR etc.) of said IBL-101 monoclonal antibody or of the antibody created based on IBL-101 monoclonal antibody. Except for this paragraph, Examples, and Brief Description of the Drawings, in this specification, reference to the "IBL-101 monoclonal antibody" also includes antibodies created based on the IBL-101 monoclonal antibody, and fragments thereof, in addition to an antibody produced by the above-mentioned Amyloid β Hybridoma IBL-101.

In another embodiment, the present invention is directed to a pharmaceutical composition comprising a substance which specifically binds to 22-23 turn Aβ as an active ingredient. Herein, the "substance which specifically binds to 22-23 turn Aβ" is not limited as long as specifically binds to 22-23 turn Aβ, and is preferably a substance which specifically binds to a steric structure of a turn structure constructed from amino acids at positions 22 and 23 of Aβ, and is more preferably a substance inhibiting the function and/or aggregation of 22-23 turn Aβ. Examples of such substance include an aptamer, a polypeptide which binds to 22-23 turn Aβ, or the above-mentioned antibody which specifically binds to 22-23 turn Aβ.

The "aptamer" is a nucleic acid binding to a substance such as a protein etc. The aptamer may be an RNA or a DNA. A form of the nucleic acid may be double-stranded or single-stranded. The length of the aptamer is not limited as long as the aptamer can specifically bind to a target molecule and may be, for example, 10 to 200 nucleotides, preferably 10 to 100 nucleotides, more preferably 15 to 80 nucleotides, and still more preferably 15 to 50 nucleotides. The aptamer can be selected using the method well-known to a person skilled in the art, and for example, the SELEX method (Systematic Evolution of Ligands by Exponential Enrichment) (Tuerk, C. and Gold, L. (1990), Science, 249:505-510) can be used.

"Polypeptide which binds to Aβ having a turn structure at amino acid positions 22 and 23 of Aβ (22-23 turn Aβ)" is a polypeptide which binds to 22-23 turn Aβ, and the binding of the polypeptide to 22-23 turn Aβ results in inhibition of aggregation of 22-23 turn Aβ and/or inhibition of the original function (neural toxicity etc.) of 22-23 turn Aβ. From the results of an experiment in the present specification, it is shown that 22-23 turn Aβs bind to each other to form a trimer. Thus, examples of the polypeptide which binds to 22-23 turn Aβ include a mutant and an analogue of 22-23 turn Aβ (for example, P3-Aβ42, E22P-Aβ42, and Aβ-lactam) or its partial peptide. For example, a polypeptide which binds to 22-23 turn Aβ can be obtained by making such mutant, analogue or partial peptide, and selecting a substance which binds to 22-23 turn Aβ. These peptides may be accordingly modified in order to improve stability or to promote inhibitory activity.

The pharmaceutical composition of the present invention may be prepared in any formulation as long as it can be administered to a patient. Formulation of a composition for parenteral administration includes, for example, injectable form, nose drops, suppositories, patches, ointments etc., and preferably is injectable. A dosage form of the medicament of the present invention includes, for example, solution or lyophilized formulation. When the medicament of the present invention is used as injectable form, if necessary, additives, for example, solubilizer such as propylene glycol and ethylenediamine, buffers such as phosphate, tonicity agents such as sodium chloride and glycerin, stabilizers such as sulfite, preservatives such as phenol, soothing agents such as lidocaine (see "Pharmaceutical Additives Dictionary (*Iyakuhin Tenkabutsu Jiten*)", YAKUJI NIPPO LIMITED and "Handbook of Pharmaceutical Excipients Fifth Edition" APhA Publications) can be added. When the therapeutic agent or the preventive agent of the present invention is used as injectable form, examples of a storage container include ampoules, vials, prefilled syringes, cartridges for pen-type injectors, and bags for intravenous drip and the like.

The pharmaceutical composition of the present invention can be used as a therapeutic agent of a disease which is developed or exacerbated by 22-23 turn Aβ. For example, such disease includes Alzheimer's disease.

In another aspect, the present invention is directed to a kit for measuring 22-23 turn Aβ, including a substance which specifically binds to 22-23 turn Aβ. For example, the kit of the present invention can be based on the known method using an antibody molecule. Such method includes, for example, ELISA, immunochromatography, radioimmunoassay, immunohistochemical method, or Western blot. As a sample of the present kit, for example, collected from a subject as a biopsy a tissue sample or a liquid sample can be used. The sample is not limited as long as it can be used in immunological measurement of the present invention, and includes, for example, a tissue, blood, plasma, serum, a lymph fluid, urine, a serous fluid, a spinal fluid, a joint fluid, an aqueous humor, a lacrimal fluid, saliva or fractionated or treated sample thereof, and preferably is a tissue (particularly, a brain tissue) or blood. Analysis using the present kit can be performed qualitatively, quantitatively or semiquantitatively.

Preferably, the substance which specifically binds to 22-23 turn Aβ in the kit of the present invention is an antibody which specifically binds to 22-23 turn Aβ, more preferably, the IBL-101 monoclonal antibody. As long as the antibody binds to 22-23 turn Aβ, there is no limitation to a structure, a size, an immunoglobulin class and an origin thereof. The kit of the present invention may include an isolated nucleic acid encoding an amino acid sequence of the antibody which specifically binds to 22-23 turn Aβ, a vector including the nucleic acid, and a cell having the vector.

The substance which specifically binds to 22-23 turn Aβ may bind to detectable labels such as radioactive labels such as $^{32}P$, $^{3}H$, $^{125}I$ and $^{14}C$; enzymes such as β galactosidase, peroxidase, alkaline phosphatase, glucose oxidase, lactic acid oxidase, alcohol oxidase, monoamine oxidase and horseradish peroxidase; coenzymes or prosthetic groups such as FAD, FMN, ATP, biotin and hem; fluorescent labels such as fluorescein derivatives (fluorescein isothiocyanate (FITC), fluorescein thiofulbamil etc.), rhodamine derivatives (tetramethylrhodamine, trimethylrhodamine (RITC), Texas Red, rhodamine 110 etc.), Cy dyes (Cy3, Cy5, Cy5.5, Cy7), Cychrome, Spectrum Green, Spectrum Orange, propidium iodide, allophycocyanin (APC) and R-phycoerythrin (R-PE); bioluminescent labels such as luciferase; or luminol derivatives such as luminol, isoluminol and N-(4-aminobutyl)-N-ethylisoluminol ester; acridinium derivatives such as N-methylacridinium ester and N-methylacridiniumacylsulfonamide ester; chemiluminescent labels such as lucigenin, adamantyldioxetan, indoxyl derivatives and ruthenium complex; metals such as gold colloid.

The kit of the present invention is not limited as long as it includes the substance which specifically binds to 22-23 turn Aβ. For example, a reagent contained in the kit of the present invention may be solid, gel or liquid. The substance which specifically binds to 22-23 turn Aβ may be contained in, or fixed to a resin, a membrane, a film, a container etc., or may be dissolved in a solvent. The kit of the present invention, if necessary, may include color developing reagent, reagent for stopping reaction, standard antigen reagent, reagent for pretreatment of sample, blocking reagent and the like. The kit of the present invention may include, for example, plates, tubes, chips (for example, protein chips, labochips etc.), beads, membranes, absorbents and/or particles, containing nitrocellulose, sepharose, nylon, vinylon, polyester, acryl, polyolefin, polyurethane, rayon, polynosic, cupra, lyocell, acetate, polyvinylidene difluoride, silicon rubber, latex, polystyrene, polypropylene, polyethylene, polyvinyl chloride, polyvinylidene chloride, polyvinyl acetate, fluorine-processed resin, aABS resin, AS resin, acryl resin, polymer alloy, glass fiber, carbon fiber, glass, gelatin, polyamino acid, and/or magnetism-sensitive material.

For example, the kit of the present invention includes a kit comprising a plate on which an antibody which specifically binds to 22-23 turn Aβ is immobilized, biotin-labeled anti-Aβ rabbit polyclonal antibody solution, streptavidin POD solution, washing liquid, TMB reagent, 2M HCl, and E22P-Aβ42, or a kit comprising an antibody which specifically binds to 22-23 turn Aβ, anti-Aβ mouse monoclonal antibody-bound gold colloid, rabbit immunoglobulin-bound gold colloid, and a test plate.

Also, the present invention is directed to a diagnostic agent for Alzheimer's disease comprising a substance which specifically binds to 22-23 turn Aβ (preferably, an antibody which specifically binds to 22-23 turn Aβ, more preferably IBL-101 monoclonal antibody). For example, when used ex vivo, the diagnostic agent of the present invention may have components according to the above-mentioned kit for measuring 22-23 turn Aβ comprising a substance which specifically binds to 22-23 turn Aβ. Alternatively, the diagnostic agent of the present invention may be optimized for diagnostic imaging. When the diagnostic agent of the present invention is used for diagnostic imaging, the substance which specifically binds to 22-23 turn Aβ contains a label substance, or is bound to a label substance. As the label substance, for example, the substance well-known to a person skilled in the art such as radioisotope can be used. Preferably, the label substance is a positron emission radioisotope or a γ-ray radiating isotope, and is not limited but include $^{131}$I, $^{123}$I, $^{124}$I, $^{86}$Y, $^{62}$Cu, $^{64}$Cu, $^{111}$In, $^{67}$Ga, $^{68}$Ga, $^{99m}$Tc, $^{94m}$Tc, $^{18}$F, $^{11}$C, $^{13}$N, $^{15}$O and $^{75}$Br. When used for diagnostic imaging, the substance which specifically binds to 22-23 turn Aβ of the diagnostic agent of the present invention is preferably a polypeptide which binds to 22-23 turn Aβ, or an antibody which specifically binds to 22-23 turn Aβ (more preferably, a chimeric antibody, a humanized antibody or a human antibody), and more preferably the IBL-101 monoclonal antibody. When used for diagnostic imaging, the diagnostic agent of the present invention may be in a pharmaceutically acceptable formulation suitable for administration to a human, and may include physiologically acceptable additives, for example, pharmaceutically acceptable diluents, buffers, solubilizers, soothing agents, solvents, stabilizers or antioxidants. A dose of the diagnostic agent of the present invention can be appropriately selected depending on a target site, diagnostic imaging method to be employed, age, sex and other conditions of a patient, and a severity of a disease.

As used herein, "XNY" (X and Y indicate single letter amino acid code; N indicates a natural number) means that the amino acid X at position N is substituted with an amino acid Y, "Aβp-q" (p and q indicate a natural number) means a peptide consisting amino acids from position p to position q of Aβ. For example, E22P-Aβ42 indicates Aβ42 in which glutamic acid at position 22 is substituted with proline, and G9C, E22P-Aβ9-35 indicates a peptide consisting of amino acids from position 9 to 35 of Aβ, in which glycine at position 9 is substituted with cysteine and glutamic acid at position 22 is substituted with proline.

Effect of the Invention

Since the antibody of the present invention can specifically bind to 22-23 turn Aβ, the antibody can specifically detect 22-23 turn Aβ, or can inhibit function of 22-23 turn Aβ. Therefore, the antibody can be utilized in diagnosis based on an expression amount of 22-23 turn Aβ as an index and can be used as a therapeutic agent or a preventive agent for a disease in which expression of 22-23 turn Aβ contributes to the onset or exacerbation.

BRIEF DESCRIPTION OF THE DRAWINGS

In FIG. 10C, CBB indicates results of staining of a membrane with Coomassie Blue. In FIG. 10E, "High-molecular weight-aggregates" indicates a high-molecular weight aggregate of Aβ and, "Monomer" indicates a monomer of Aβ. In all photographs of FIG. 10, a numerical value on a right side of each photograph represents a molecular mass (kDa).

DESCRIPTION OF EMBODIMENTS

Figure 1:
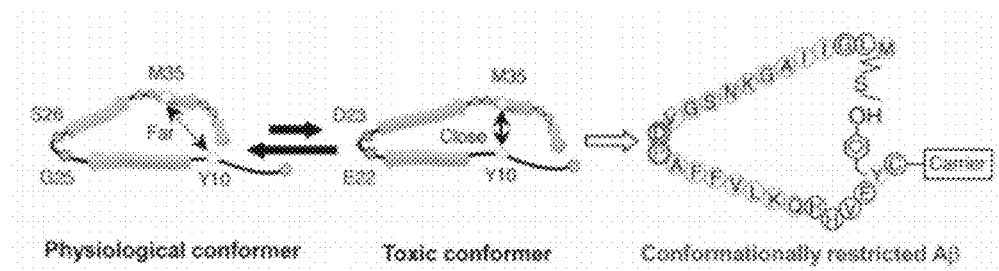
FIG. 1 is a view schematically showing a steric structure (turn structure) of Aβ42.

1. Preparation of Antibody which Specifically Recognizes 22-23 Turn Aβ

The antibody of the present invention can be prepared, for example, by immunizing non-human mammals or birds with 22-23 turn Aβ, if necessary, together with an immunostimulant (for example, mineral oil or aluminum precipitate and heat-killed bacterium or lipopolysaccharide, Freund's complete adjuvant, or Freund's incomplete adjuvant etc.).

The immunogen is preferably E22P-Aβ42, Aβ-lactum (22K-23E) and P3-Aβ42, and more preferably E22P-Aβ42. The immunogen can be obtained as a recombinant protein obtained by introducing a gene DNA, preferably a cDNA encoding the objective substance into a cell strain of bacterium, yeast, or animal cell, and then expressing the DNA. The immunogen can be also obtained as a synthetic protein.

For example, the immunogen used in preparation of the antibody of the present invention can be obtained by introducing an expression vector including a cDNA encoding the immunogen into *Escherichia coli*, yeast, insect cell, animal cell etc., and then expressing the cDNA. Alternatively, the immunogen can be made by chemical synthesis using a Fmoc method or a Boc method etc. For example, a peptide having a desired amino acid sequence can be obtained by immobilizing a C-terminal amino acid of the immunogen onto a polystyrene carrier, and repeating a step of binding an amino acid protected with 9-fluorenylmethyloxycarbonyl group (Fmoc group) or tert-butoxycarbonyl group (Boc group) by using condensing agent such as diisopropylcarbodiimide (DIC) etc., a step of washing, and a step of deprotecting the peptide. Alternatively, the immunogen can be also synthesized using an automatic peptide synthesizer. Such peptide synthesizer includes PSSM-8 (Shimadzu Corporation); Model 433A Peptide Synthesizer (Applied Biosystems); ACT396Apex (Advanced Chemtec) and the like.

When a polypeptide having substantially the same amino acid sequence as that of Aβ is used as the immunogen, for example, a synthetic oligonucleotide site mutation introduction method (gapped duplex method), a method for randomly introducing point mutation by treatment with nitrous acid or sulfurous acid, a method for making a deletion mutant with a Ba131 enzyme etc., a cassette mutation method, a linker scanning method, a miss-incorporation method, a mismatch primer method, or a DNA segment synthesizing method can be used.

The immunogen is administered alone or with a carrier and a diluent to an animal to be immunized at a site where the administration can stimulate antibody production. Upon administration, in order to enhance ability of antibody production, a complete Freund's adjuvant or an incomplete Freund's adjuvant may be co-administered. The animal to be immunized is not limited as long as the animal can be used for creating a hybridoma, such as mouse, rat, hamster, guinea pig, rabbit, dog, monkey, sheep, goat, chicken and duck, preferably is mouse or rat, and more preferably is mouse.

Administration of immunogen to animal can be performed, for example, by subcutaneous injection, intraperitoneal injection, intravenous injection, intradermal injection, intramuscular injection or pad injection, preferably subcutaneous injection or intraperitoneal injection. The amount of the immunogen to be used is not limited as long as being able to produce antibody and is preferably 0.1 to 1,000 μg, more preferably 1 to 500 μg, and more further preferably 10 to 100 μg. Immunization can be performed once, or a few times at an appropriate interval. Usually, around 2 to 10 times immunization in a total are performed by one immunization per every 1 to 6 weeks preferably 2 to 5 times immunization in a total are performed by on immunization per every 1 to 5 weeks, and more preferably three times immunization in a total are performed by on immunization per every 3 weeks. One to two weeks after the last immunization, blood sample is collected from an orbit or a tail vein of immunized animal, and antibody titer is measured using the serum obtained from the blood sample. The measurement of antibody titer can be performed by methods well-known in the art. Fr example, a radioisotope immunoassay method (RIA method), a solid phase enzyme immunoassay method (ELISA method), a fluorescent antibody method, a passive hemocyte agglutination reaction method, and preferably an ELISA method can be employed. The antibody of the present invention can be obtained by purification from serum of animal exhibiting a sufficient antibody titer.

A monoclonal antibody can be obtained by culturing a hybridoma obtained by fusing an antibody-producing cell obtained from an immune sensitized animal immunized by the above-mentioned method with a myeloma cell. As the method for fusion, a method by Milstein et al. (Galfre, G. & Milstein, C. (1981), Methods Enzymol., 73: 3-46) can be employed.

An antibody-producing cell to be used can be collected from spleen, pancreas, lymphatic node or peripheral blood, and preferably spleen, of mouse or rat which was immunized by the above-mentioned method and exhibited a sufficient antibody titer in serum.

The myeloma cell to be used is not limited as long as it is derived from a mammal such as mouse, rat, guinea pig, hamster, rabbit or human and can be proliferated in vitro. For example, such cell includes P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8. 653 (653) (J. Immunol., 123, 1548, 1979), Sp2/O-Ag14 (Sp2/O) (Nature, 276, 269, 1978), Sp2/O/FO-2 (FO2) (J. Immunol. Methods, 35, 1, 1980) etc., preferably is a cell derived from the same animal species as that of an antibody-producing cell, more preferably is a cell derived from the same animal phylesis as that of an antibody-producing cell. For example, a mouse-derived myeloma cell is preferably P3U1 or P3X63-Ag8-653. A myeloma cell can be preserved by freezing or can be maintained by subculturing in a common medium with equine, leporid or fetal serum. As the myeloma cell to be used in cell fusion, a cell at a exponential growth phase is preferable.

A method for fusing an antibody-producing cell and a myeloma cell to form a hybridoma includes a method using polyethylene glycol (hereinafter, referred to as "PEG") etc., a method using Sendai virus, and a method using an electric fusing apparatus.

For example, in the case of using PEG, an antibody-producing cell obtained according to the above-mentioned method and a myeloma cell are washed with a medium, PBS etc., and then spleen cells and myeloma cells are suspended in an appropriate medium or buffer including a cell aggregating medium such as 30 to 60% PEG (average molecular weight 1000 to 6000) etc. at a mixing ratio of 1:2 to 10:1 (preferably, 5:1 to 10:1), followed by reaction for around 30 seconds to 3 minutes at a temperature of about 25 to 37° C. and at a pH of 6 to 8. After the reaction, PEG solution is removed, and cells are re-suspended in a medium, which is then seeded in a cell well plate to continue culturing.

Selection of a hybridoma cell producing monoclonal antibody can be performed according to known methods or methods based on the known methods. Usually, selection of a hybridoma cell can be performed by using selective growth of hybridoma in medium for an animal cell with HAT (hypoxanthine-aminopterin-thymidine). As medium for selection and breeding, any medium may be used as long as hybridoma cell can be grown therein. For example, RPMI 1640 medium containing 1 to 20%, preferably 10 to 20 fetal bovine serum, a GIT medium including 1 to 10% fetal bovine serum (Wako Pure Chemical Industries, Ltd.) or serum-free medium for hybridoma culture (SFM-101, Nissui Pharmaceutical Co., Ltd.) can be used. Temperature of the culture is usually 20 to 40° C., and preferably about 37° C. Duration of the culture is usually 5 days to 3 weeks, and preferably 1 week to 2 weeks. The culture can be usually performed under 5% $CO_2$.

After the culture, supernatant is collected and used for selection of a clone which specifically binds to antigen protein, and weakly binds to proteins other than objective antigen protein by ELISA etc. By repeating a limiting dilution method once to 5 times, preferably 2 to 4 times, a single cell is obtained from such clone and then a cell stably exhibiting a high antibody titer can be selected from single cells. The antibody which specifically binds to 22-23 turn Aβ of the present invention can be obtained by repeating screening of selection of a clone which strongly binds to all Aβ mutants that are more likely to take a β-turn structure at positions 22 and 23 (E22Q-Aβ42, E22G-Aβ42, E22K-Aβ42, E22P-Aβ42, and D23N-Aβ42) (K. Murakami et al. (2003), J. Biol. Chem., 278:46179-46187) (FIG. 1) according to the ability to bind to the Aβ mutants. For example, an antibody recognizing 22-23 turn Aβ can be obtained by measuring binding of 22-23 turn Aβ to antibodies obtained by the above-mentioned method etc., and then selecting an antibody with high binding activity etc. A binding constant ($K_a$) in binding of the antibody which specifically binds to 22-23 turn Aβ of the present invention to 22-23 turn Aβ is, for example, at least $10^7$ $M^{-1}$, preferably at least $10^8$ $M^{-1}$, and more preferably at least $10^9$ $M^{-1}$. Such binding constant is further more preferably $10^{10}$ $M^{-1}$, $10^{11}$ $M^{-1}$, $10^{12}$ $M^{-1}$ or more, for example, $10^{13}$ $M^{-1}$ or more. The antibody which specifically binds to 22-23 turn Aβ can be obtained by selecting an antibody which does not recognize Aβ without turn structure at amino acid positions 22 and 23 from antibodies which recognizes 22-23 turn Aβ obtained in the above by using a method well-known to a person skilled in the art.

Alternatively, a hybridoma producing the antibody of the present invention can be obtained from hybridoma cell line Amyloid β Hybridoma IBL-101 (date of deposit is Oct. 14, 2009, registration number is PERM BP-11290) deposited at National Institute of Advanced Industrial Science and Technology, Incorporated administrative agency, International Patent Organism Depository (Tsukuba Center Central 6, 1-1-1 Higashi, Tsukuba-shi, Ibaraki, Japan).

The monoclonal antibody of the present invention can be obtained by culturing the hybridoma obtained as described above in vitro, and then purifying culture fluid. Alternatively, the monoclonal antibody of the present invention can be also obtained by transplanting a hybridoma into a syngeneic animal or an immunodeficient animal to which pristane has been intraperitoneally administered in advance, and then generating ascites, which is then collected and purified.

The resulting antibody can be purified to be uniform. Antibody can be separated or purified by using common method of separation or purification used for proteins. For example, an antibody can be separated or purified by appropriately selecting or combining a chromatography column such as affinity chromatography, a filter, ultrafiltration, salting out, dialysis, SDS polyacrylamide gel electrophoresis, isoelectric point electrophoresis etc. (Antibodies: A Laboratory Manual., Ed Harlow and David Lane, Cold Spring Harbor Laboratory, 1998). As a column for affinity chromatography, for example, Protein A column, and Protein G column can be used. For example, the Protein A column includes Hyper D, POROS, Sepharose F. F. (Amersham Biosciences). In the case of IgY and IgM, a column using mercaptopyridine as a ligand can be used. Alternatively, E22P-Aβ42 immobilized column, ion exchange chromatography, hydrophobic interaction chromatography etc. can be also used regardless of a class of an antibody. Purification of a monoclonal antibody can be performed, for example, by collecting an IgG fraction using a Protein A column or a Protein G column etc. after centrifugation.

2. Preparation of Human Chimeric Antibody, Humanized Antibody, Human Antibody (1) Human-Type Chimeric Antibody The human chimeric antibody of the present invention can be obtained by preparing DNAs encoding VH and VL of a non-human animal-derived monoclonal antibody which binds to 22-23 turn Aβ and which inhibits the function of 22-23 turn Aβ, and then binding the DNA to cDNA coding a constant region of a human-derived immunoglobulin, and inserting the combined DNA into an expression vector, which is then transformed into a suitable host cell, and expressing the combined DNA (Morrison, S. L. et al., Proc. Natl. Acad. Sci. USA, 81, 6851-6855, 1984).

The DNAs encoding VH and VL of a non-human animal-derived monoclonal antibody can be obtained, for example, by following method. Extracting mRNA from animal B cell which produces the monoclonal antibody by method well-known to a person skilled in the art, for example, by preparing RNA with guanidine-ultracentrifugation method (Chirgwin, J. M. et al., Biochemistry, 18, 5294-5299, 1979), or AGPC method (Chomczynski, P et al., Analytical Biochemistry, 162, 156-159, 1987) etc., and then purifying mRNA with mRNA Purification Kit (Pharmacia, Takara Bio, Inc.). By using the extracted mRNA and an oligo dT primer, cDNA is generated, which is then inserted into a vector. A cDNA encoding a non-human animal-derived monoclonal antibody can be isolated from cDNAs inserted into the vector by using a probe coding a portion of a non-human animal-derived monoclonal antibody. By determining a nucleotide sequence of an isolated cDNA, DNA sequences encoding objective VH and VL can be obtained.

Other methods for obtaining DNAs encoding VH and VL of a non-human animal-derived monoclonal antibody include a following method. The coding region of VH or VL is amplified by PCR method using a cDNA obtained as described above and primers which can amplify VH or VL (for example, when the non-human animal is mouse, a primer hybridizing with a mouse H chain constant region (C region) and a primer hybridizing with a conserved sequence of a mouse L chain γ chain constant region etc. (R. Orlandi et al. (1989), Proc. Natl. Acad. Sci. USA, 86, 3833)). Alternatively, the coding region VH or VL is amplified by a RT-PCR method using mRNA extracted from animal B cell producing monoclonal antibody and said primers which can amplify VH or VL. An objective DNA fragment is extracted from the resulting PCR product. Extraction of an objective DNA fragment can be performed, for example, by excising a band showing a size of an objective DNA after agarose gel electrophoresis, and extracting a DNA from the gel slice. DNA sequences encoding objective VH and VL can be obtained by digesting the vector and the extracted DNAs with a restriction enzyme, and then inserting the digested DNAs into the vector, and determining a DNA sequence encoded by the inserted DNA.

As CH and CL of human antibody CH and CL in a human chimeric antibody, any CH and CL of human antibody can be used. For example, CH of human γ1, γ2 and CL of human κ can be used. As genes encoding CH and CL of a human antibody, chromosomal DNA or cDNA can be used. A vector expressing the chimeric antibody of the present invention can be created, for example, by binding DNAs encoding VH and VL of a non-human animal-derived monoclonal antibody obtained in the above with DNAs encoding CH and CL of a human antibody, respectively, and inserting the combined DNA into an expression vector for an animal cell.

An enhancer and a promoter used in expression of a human chimeric antibody include an enhancer and a promoter of an immunoglobulin gene itself, or an enhancer and a promoter for non-immunoglobulin. For example, when the non-human animal is mouse, an expression regulating system of immunoglobulin gene is common between mouse and human, and thus a recombinant DNA can be prepared to include a mouse or human enhancer sequence located between J gene and C gene.

As the expression vector for an animal cell, for example, pSV2-gpt (R. C. Mulligan and P. Berg (1980), Science, 209, 1422) can be used. Genes encoding an H chain and an L chain of the human chimeric antibody of the present invention prepared as described above may be inserted into the same vector, or may be inserted into different vectors.

(2) Humanized Antibody

The humanized antibody of the present invention can be obtained by constructing a DNA encoding a V region in which amino acid sequences encoding CDRs of VH and VL of a non-human animal-derived monoclonal antibody which specifically binds to 22-23 turn Aβ are transplanted into FRs of VH and VL of a human antibody, respectively, binding the constructed DNA with cDNA coding constant region of human-derived immunoglobulin, inserting the DNA into an expression vector, transforming the vector into a suitable host cell, and expressing the DNA (see L. Rieohmann et al. (1988), Nature, 332, 323; Kettleborough, C. A. et al. (1991), Protein Eng., 4, 773-783; Clark M., (2000), Immunol. Today., 21, 397-402).

Each of amino acid sequences of CDRs from a non-human animal-derived monoclonal antibody can be obtained by comparing amino acid sequences predicted from DNA sequences encoding VH and VL of the non-human animal-derived monoclonal antibody (for example, IBL-101 monoclonal antibody) obtained as described above, with entire amino acid sequences of VH and VL of a known antibody. Amino acid sequences of a known antibody can be obtained, for example, from amino acid sequences of antibodies registered in database such as Protein Data Bank etc.

FRs from a human antibody are not limited as long as transplanted humanized antibody exerts the effect of the present invention, and are preferably human antibody's FRs which result in a humanized antibody with V region which has a similar steric structure to a V region of a non-human animal-derived monoclonal antibody to be used, or human antibody's FRs having high homology in amino acid sequence to FR of a non-human animal-derived monoclonal antibody to be used. Whether or not a V region of a humanized antibody comprising selected FRs from a human antibody has a similar steric structure to a V region of an original non-human animal-derived monoclonal antibody can be determined, for example, by predicting a steric structure by computer modeling based on information of a DNA sequence of a V region comprising selected FRs from a human antibody, and comparing the predicted steric structure with a steric structure of a V region of an original non-human animal-derived monoclonal antibody used. Amino sequences of FRs from a non-human animal-derived monoclonal antibody to be used can be obtained from information of amino acid sequences predicted from DNA sequences encoding VH and VL and an amino acid sequence of CDR obtained as described above. Alternatively, by introducing mutation into the amino acid sequence of FR from a human antibody, a steric structure of V region of a humanized antibody can be similar to that of V region of an original non-human animal-derived monoclonal antibody to be used, or human antibody FRs can have high homology in an amino acid sequence to FRs of an original non-human animal-derived monoclonal antibody to be used.

A DNA sequence encoding a V region of a humanized antibody is designed as a DNA sequence corresponding to a combination of amino acid sequences of CDR of a non-human animal-derived monoclonal antibody and amino acid sequences of FR of a human antibody. The DNA encoding a V region of a humanized antibody can be made by the method well-known to a person skilled in the art based on the designed DNA sequence. For example, the DNA can be obtained by chemical synthesis of around 100 bp DNA fragments based on the designed DNA, and amplification of the DNA fragments by PCR. Alternatively, the DNA can be also obtained by binding around the 100 bp DNA fragments using an enzyme such as ligase etc., performing PCR using primers encoding sequences of both ends of the designed DNA sequence encoding the V region of the humanized antibody, and extracting a DNA fragment having a desired length. Further, the DNA encoding the V region of the humanized antibody in PCR can be also obtained by the method known as CDR grafting. Alternatively, the DNA encoding the V region of the humanized antibody can be also obtained by introducing DNAs encoding CDRs into a DNA of a V region of a human antibody by site-specific mutation. Site-specific mutation can be performed using, for example, Gene Taylor-Site Directed Mutagenesis System (Invitrogen), Transformer Site-Specific Mutagenesis Kit (Clontech) and Site Directed Mutagenesis System (Takara Bio, Inc.) according to protocols provided with the kit.

As human antibody CH and CL of a humanized antibody, CH and CL from any human antibody can be used. For example, CH of human γ1, γ2 and CL of human κ can be used. Genes encoding CH and CL of a human antibody can be obtained from a chromosomal DNA or a cDNA. A vector expressing the humanized antibody of the present invention can be made, for example, by binding the DNA encoding V regions of the humanized antibody obtained in the above to DNAs encoding CH and CL of a human antibody, respectively, and inserting the combined DNA into an expression vector for an animal cell.

An enhancer and a promoter used in expression of a humanized antibody include an enhancer and a promoter of an immunoglobulin gene itself, or an enhancer and a promoter for non-immunoglobulin. For example, when the non-human animal is mouse, an expression regulating system of immunoglobulin gene is common between mouse and human, and thus a recombinant DNA can be prepared to include a mouse or a human enhancer sequence located between J gene and C gene.

As the expression vector for an animal cell, for example, pSV2-gpt (R. C. Mulligan and P. Berg (1980), Science, 209, 1422) can be used. Genes encoding an H chain and an L chain of the humanized antibody of the present invention prepared as described above may be inserted into the same vector, or may be inserted into different vectors.

A non-human animal-derived monoclonal antibody which is used in making the above mentioned human chimeric antibody or humanized antibody is not limited as long as it is an antibody which specifically binds to 22-23 turn Aβ, and is preferably a mouse monoclonal antibody.

(3) Human Antibody

The human antibody can be obtained by utilizing a human antibody phage library or a human antibody-producing transgenic mouse (Tomizuka et al. (1997), Nature Genet., 15, 146-156).

The human antibody phage library is a library of phages wherein Fab or scFv of human antibody is presented on surface of phage as a fused protein. The library can be obtained by introducing VH genes and VL genes from an antibody gene pool with a variety of sequences derived from a human B cell into phage genes. Such human antibody phage library includes a naïve non-immune library obtained by amplifying VH genes and VL genes of antibodies using peripheral blood lymphocyte and the like from healthy human by RT-PCR, and preparing a library the genes (Cambridge Antibody Technology; Medical Research Council; Diax etc; a synthetic library obtained by selecting a particular antibody gene which is functional in a human B cell, replacing an antigen-binding region such as a CDR 3 region of a V gene fragment with oligonucleotides encoding random amino acid sequences of suitable length, and preparing a library (Bioinvent; Crucell; Morphsys; and an immune library which is a library made from a lymphocyte of a patient of cancer, autoimmune disease or infectious disease or from a person inoculated with a subject antigen as a vaccine.

For example, a naive human antibody phage library can be made by following method. Using mRNAs prepared from peripheral blood of a human, cDNAs of V gene are prepared by using primers specific for constant regions of γ, μ, κ or λ chains of immunoglobulin, then each of V genes is synthesized using a set of DNA primers specific for respective V gene family, and synthesized genes are connected by PCR using a linker DNA encoding a linker peptide such as (Gly4Ser)$_3$ to obtain scFv genes. The obtained scFv genes are inserted into phagemid vectors such as pCANTAb5E by using restriction enzyme sites on both ends for introduction into vector, the vectors are transformed into *Escherichia coli*, which is them infected with a helper phage to rescue.

When a human antibody phage library is utilized, for example, a desired clone can be obtained by immobilizing E22P-Aβ42 as a target onto a solid phase, reacting an antibody phage library to the E22P-Aβ42, washing and removing unbound phages, and recovering bound phages (panning). Amplification of the resulting phages and repeated application of the amplified phages to further panning can increase probability of success of obtaining intended clone. By analyzing a VH gene and a VL gene of the resulting clone, a complete human antibody having these gene sequences can be made.

A human antibody-producing transgenic mouse is a mouse in which an endogenous Ig gene is knocked out and an immunoglobulin (Ig) gene of a human antibody is introduced. The human antibody-producing transgenic mouse can be obtained, for example, by following method. By colcemid (spindle fiber formation inhibitor)-treatment of a human-mouse hybrid cell for 48 hours, a microcell in which one to a few chromosomes are wrapped with a nuclear membrane is formed. An isolated microcell and a chromosome receiving cell (mouse ES cell) are fused by using polyethylene glycol in the presence of cytochalasin B to make a microcell hybrid ES cell, and obtained cell is injected into a mouse germ.

By immunizing a human antibody-producing transgenic mouse as an animal to be immunized with an immunogen according to the above described antibody preparing method, an antibody which specifically binds to 22-23 turn Aβ can be obtained.

3. Preparation of Antibody Fragment

A fragment of the antibody of the present invention (F(ab')$_2$, Fab', Fab, scFv, dsFv or a polymer thereof, Diabody, or a peptide including CDR) can be prepared by the following method.

The F(ab')$_2$ fragment of the present invention can be obtained by treating an IgG antibody which specifically binds to 22-23 turn Aβ with a protease pepsin to cut at amino acid position 234 of an H chain as an antibody fragment having antigen binding activity of a molecular weight of about 100 thousands. Alternatively, the F(ab')$_2$ fragment of the present invention can be obtained by thioether-binding or disulfide-binding of Fab' s described later.

The Fab' fragment of the present invention can be obtained by treating F(ab')$_2$ which specifically binds to 22-23 turn Aβ obtained in the above with a reducing agent, dithiothreitol. Alternatively, the Fab' fragment of the present invention can be obtained by inserting a DNA encoding Fab' of the antibody which specifically binds to 22-23 turn Aβ of the present invention into an expression vector, transforming the vector into a host cell, and expressing the DNA.

The Fab fragment of the present invention can be obtained by treating the antibody which specifically binds to 22-23 turn Aβ of the present invention with a protease papain to cut at amino acid position 224 of an H chain as an antibody fragment having antigen binding activity of a molecular weight of about 50 thousands, in which an about half part of N-terminal side of an H chain and an entire of an L chain are bound through a disulfide bond. Alternatively, the Fab fragment of the present invention can be obtained by inserting a DNA encoding Fab of the antibody which specifically binds to 22-23 turn Aβ of the present invention into an expression vector, transforming the vector into a host cell, and expressing the DNA.

The scFv of the present invention can be obtained by preparing cDNAs encoding VH and VL of the antibody of the present invention which specifically binds to 22-23 turn Aβ, inserting a DNA encoding a linker sequence between these cDNAs to construct a DNA encoding scFv, inserting the DNA into an expression vector, transforming the vector into a host cell, and expressing the DNA. The length of the linker is not limited as long as VH and VL can be associated, and is preferably 10 to 20 residues, and more preferably 15 residues. A sequence of the linker is not limited as long as it does not inhibit folding of a polypeptide chain of 2 domains of VH and VL, and is preferably a linker consisting of glycine and/or saline, preferably GGGGS (G: glycine, S-serine) or a repeat sequence thereof.

The dsFv of the present invention can be obtained by substituting one amino acid residue in each of VH and VL with a cysteine residue by site-specific mutation, and binding VH and VL through a disulfide bond between the cysteine residues. The amino acid to be substituted is not limited as long as it is an amino acid residue having no influence on antigen binding based on a steric structure.

The Diabody of the present invention can be obtained by constructing a DNA of said scFV to have a linker of 8 residues or less (preferably, 5 residues) of amino acid, inserting the DNA into an expression vector, transforming the vector into a host cell, and expressing the DNA. Bispecific Diabody can be obtained by making scFv by combining different 2 kinds of DNAs encoding VH and VL of scFvs.

The peptide including CDR of the present invention can be obtained by constructing a DNA encoding an amino acid sequence of CDR of VH or VL of the antibody which specifically binds to 22-23 turn Aβ of the present invention, inserting the DNA into an expression vector, transforming the vector into a host cell, and expressing it.

4. Pharmaceutical Composition

The antibody obtained by the above-mentioned methods is purified, if necessary, and thereafter, are formulated into preparations according to the conventional method, which can be used as a preventive agent and/or a therapeutic agent of various diseases etc. For example, injectable preparations include forms such as intravenous injectable preparations, subcutaneous injectable, intradermal injectable, intramuscular injectable preparations, and dripping injectable preparations. Such injectable preparations can be prepared, for example, by dissolving, suspending, or emulsifying said antibody etc. in a sterile aqueous or oily liquid usually used in injectable preparations, according to the known method. As an aqueous liquid for injection, for example, an isotonic solution including a physiological saline, glucose, sucrose, mannitol, or other supplement etc. can be used. The aqueous liquid can be used with a suitable solubilizer, for example, an alcohol (e.g. ethanol), a polyalcohol (e.g. propylene glycol, polyethylene glycol) and a nonionic surfactant [e.g. Polysorbate 80, Polysorbate 20, HCO-50 (polyoxyethylene (50 mol) adduct of hydrogenated castor oil)]. As an oily liquid, for example, a sesame oil, and a soybean oil can be used. The oily liquid can be used with benzyl benzoate and benzyl alcohol as a solubilizer. A prepared injection solution is usually filled into suitable ampoules, vials, or syringes. Suppositories used in rectal administration are prepared by mixing the above-mentioned antibody with normal bases for nose drops, or bases for suppositories. By adding suitable excipients to the above-mentioned antibody, lyophilized preparations are prepared, which can be dissolved in injection solvent or a physiological saline upon use to obtain injection solutions. Generally, oral administration of a protein such as an antibody is considered to be difficult due to degradation in a digestive organ, but there is a possibility of oral administration by design of an antibody fragment or a modified antibody fragment and a dosage form. Preparations of oral administration include capsules, tablets, syrups, and granules etc.

It is suitable that the above parenteral pharmaceutical composition is prepared into a dosage form of an administration unit so as to be compatible with a dose of an active ingredient. As a dosage form of such administration unit, injectable preparations (ampoules, vials, prefilled syringes), nose drops, and suppositories are exemplified, and usually 5 to 500 mg, preferably 5 to 100 mg in the case of injectable preparations, or 10 to 250 mg in the case of other dosage form, of the said antibody etc. are contained per each administration unit dosage form.

The route of administration of the pharmaceutical composition of the present invention is not limited as long as the desired treating effect or preventing effect can be obtained. Administration routes include oral administration, intraoral administration, tracheobronchial administration, subcutaneous administration, intramuscular administration, intravascular (intravenous) administration etc. Preferably, the pharmaceutical composition is administered into a blood vessel (for example, intravenous, intracoronary). Administration of the composition of the present invention includes intravenous administration by injection or by venous dripping injection. The pharmaceutical composition of the present invention may be administered one time or may be administered continuously or intermittently. For example, the composition of the present invention can be continuously administered for 1 minute to 2 weeks. The dose of the pharmaceutical composition of the present invention is not limited as long as the desired treating effect or preventing effect is obtained, and can be appropriately determined depending on symptom, sex, age etc. A dose of the therapeutic agent or the preventive agent of the present invention can be determined, for example, by referring the AD treating effect or preventing effect. For example, when used for preventing and/or treating an AD patient, the pharmaceutical composition of the present invention is administered around once to 10 times per one month, preferably around once to 5 times per one month at usually around 0.01 to 20 mg/kg weight, preferably around 0.1 to 10 mg/kg weight, further preferably 0.1 to 5 mg/kg weight per one administration by intravenous injection. Also in the case of other parenteral administration and oral administration, an amount corresponding to said intravenous injection can be administered. When symptom is particularly severe, an amount may be increased or a frequency of administration may be increased, depending on the symptom.

5. Measurement Kit Diagnostic

Since the antibody etc. of the present invention can specifically bind to 22-23 turn Aβ, they can be used in measuring 22-23 turn Aβ in a sample solution. Since 22-23 turn Aβ is associated with the onset and exacerbation of AD, the substance which specifically binds to 22-23 turn Aβ of the present invention can be used as a diagnostic agent of an AD disease.

In the case of ex vivo measurement or diagnosis, measuring methods include labeled immunological measuring methods such as an enzyme immunoassay (EIA method), a simple EIA, an enzyme-linked immunosolvent assay (ELISA method), a radioimmunoassay (RIA method), a fluorescent immunological measuring (FIA method); immunoblotting methods such as a Western blotting; immunochromatography methods such as a gold colloid aggregating; chromatography methods such as an ion exchange chromatography, an affinity chromatography; turbidimetric analysis (TIA method); nephelometry (NIA method); colorimetric method; a latex aggregation method (LIA method); a particle counting method (CIA method); a chemiluminescent measurement method (CLIA method, CLEIA method); a precipitation reaction method; a surface plasmon resonance method (SPR method); a resonant mirror detector method (RMD method); a comparative interference method and the like.

In the case of diagnosis with administration of the substance which specifically binds to 22-23 turn Aβ into a living body, diagnosis can be performed by diagnostic imaging.

In the measurement by the EIA method, the substance which specifically binds to 22-23 turn Aβ is reacted with 22-23 turn Aβ in a sample from a subject, a labeled antibody recognizing a substance which binds to 22-23 turn Aβ is added to bound to the substance, a non-bound antibody is removed, and then formation of a complex can be measured by using a method suitable for the label substance. For example, as using the EIA method, in detecting 22-23 turn Aβ using a biotin-labeled antibody, a sample prepared by diluting a body fluid of a subject or E22P-Aβ42, and a biotin-labeled antibody solution are added to each well of a 96-well plate coated with an antibody which specifically binds to 22-23 turn Aβ which is incubated at room temperature for reaction, and then each well is washed with washing solution, followed by addition of a substrate solution (TMB) to initiate a reaction at room temperature, the reaction is stopped by adding a stopping solution (2M HCl), and absorbance at 450 nm is measured with a plate reader, thereby, 22-23 turn Aβ can be measured. A concentration of 22-23 turn Aβ in a sample can be calculated utilizing a calibration curve obtained by a standard solution. In measurement by the immunochromatography method, after a sample is bound to a labeled antibody, chromatography utilizing capillary phenomenon of a nitrocellulose membrane is performed, and 22-23 turn Aβ can be detected as binding of the sample/labeled antibody complex to solid-phased antigen-specific antibody. In the immunochromatography method, by utilizing a gold colloid as a label, binding of the solid-phased antibody and the sample/labeled antibody complex can be visually confirmed. In using the CLIA method as a chemiluminescent measuring method, an antibody which specifically recognizes 22-23 turn Aβ labeled with luminol derivative or acridinium derivative is reacted with 22-23 turn Aβ in a sample from a subject, and then an unbound antibody is removed, and thereafter, 22-23 turn Aβ can be detected from luminescence of a chemiluminescent labeled body adsorbed onto a solid phase.

In using a diagnostic imaging, the diagnosis method for the present invention can be performed by measuring the presence or the absence, localization, and/or an existence amount of 22-23 turn Aβ in a living body, by administering a substance which specifically binds to 22-23 turn Aβ, and generating an image of one or more part of the substance using diagnostic imaging apparatus (for example, scintigraphy, PET or SPECT modality). Administration of the diagnostic agent of the present invention may be local or systemic. An administration route is not particularly limited, and the diagnostic agent is administered orally or parenterally. A parenteral administration routes include subcutaneous or intraperitoneal injection or dripping, or injection or dripping into blood (intravenous or intra-arterial) or into a spinal fluid, preferably is administration into a blood.

6. Diagnosis Method and Method for Collecting Information for Diagnosis

The substance which binds to 22-23 turn Aβ (particularly, the antibody of the present invention) can be used in a method for the diagnosis of a disease caused by 22-23 turn Aβ, a method for providing information for diagnosing a disease caused by 22-23 turn Aβ, a method for monitoring the state or progression of a disease caused by 22-23 turn Aβ, and a method for determining the treating effect of a therapeutic agent on a disease caused by 22-23 turn Aβ (hereinafter, collectively named "method for diagnosing a disease caused by 22-23 turn Aβ etc."). The disease caused by 22-23 turn Aβ is preferably Alzheimer's disease.

The method for diagnosing a disease caused by 22-23 turn Aβ of the present invention includes the step of detecting 22-23 turn Aβ in a specimen, and perform diagnosis from an amount of generation of 22-23 turn Aβ as an index.

More specifically, the method for diagnosing a disease caused by 22-23 turn Aβ of the present invention can be carried out by the following steps:
a) a step of preparing a sample derived from a subject,
b) a step of contacting the sample with at least one antibody or a fragment thereof which specifically recognizes 22-23 turn Aβ,
c) a step of detecting binding of 22-23 turn Aβ to the antibody or a fragment thereof and measuring a level of 22-23 turn Aβ,
d) a step of associating the level of 22-23 turn Aβ with the presence or the absence of or severity of a disease caused by 22-23 turn Aβ.

For example, the above-mentioned method can be carried out by the ELISA method or the immunochromatography method.

The method for diagnosing a disease caused by 22-23 turn Aβ of the present invention can be carried out by the following steps:
a) a step of preparing a sample derived from a subject,
b) a step of separating 22-23 turn Aβ,
c) a step of detecting the separated 22-23 turn Aβ,
d) a step of associating a level of 22-23 turn Aβ with the presence or the absence or or an extent of a disease caused by 22-23 turn Aβ in a subject.

For example, the above-mentioned method can be carried out by using a combination of chromatography and mass spectrum.

In the above description, the "step of associating a level of 22-23 turn Aβ with the presence or the absence of or an extent of a disease caused by 22-23 turn Aβ in a subject" can include a step of determining a subject with large amount of 22-23 turn Aβ to be a patient suffering from or a patient with more severe form of disease caused by 22-23 turn Aβ.

The method for diagnosing a disease caused by 22-23 turn Aβ etc. of the present invention includes the step of detecting 22-23 turn Aβ in a sample, and can be performed using a ratio of production amount of 22-23 turn Aβ as an index. As such ratio, for example, a ratio of 22-23 turn Aβ relative to an entire Aβ amount or a ratio of 22-23 turn Aβ relative to Aβ not having turn structure at amino acid positions 22 and 23 can be utilized.

A ratio of a 22-23 turn Aβ level in a sample can be measured as a ratio of 22-23 turn Aβ relative to entire Aβ, for example, by following method:
a method comprising the steps:
a step of measuring an entire Aβ level in a sample,
a step of measuring a 22-23 turn Aβ level in a sample, and
a step of calculating a ratio of the measured 22-23 turn Aβ level relative to the measured entire Aβ level.

Therefore, the diagnosis method of the present invention may be, for example, a method for diagnosis of Alzheimer's disease comprising following steps:
a step of measuring an entire Aβ level in a sample,
a step of measuring a 22-23 turn Aβ level in a sample,
a step of calculating a ratio of the measured 22-23 turn Aβ level relative to the measured entire Aβ level, and
a step of associating the ratio of the 22-23 turn Aβ level relative to the entire Aβ level with presence or absence of or severity of Alzheimer's disease.

More specifically, a method for diagnosing a disease caused by 22-23 turn Aβ can be carried out by following steps:
a) a step of preparing a sample derived from a subject,
b) a step of contacting the sample with an antibody which specifically recognizes 22-23 turn Aβ,
c) a step of measuring a level of 22-23 turn Aβ,
d) a step of contacting the sample with an antibody which recognizes Aβ not having turn structure at amino acid positions 22 and 23 or with an antibody which recognizes Aβ,
e) a step of measuring a level of Aβ not having turn structure at amino acid positions 22 and 23 or a level of Aβ,
f) a step of calculating a ratio of an amount of 22-23 turn Aβ relative to an amount of Aβ not having turn structure at amino acid positions 22 and 23 or to an amount of Aβ, and
g) a step of associating the calculated ratio with presence or absence of or severity of a disease caused by 22-23 turn Aβ in a subject.

In the above description, an antibody which recognizes Aβ is preferably an antibody which can bind to all Aβs regardless of the presence or the absence of a turn structure.

In the above description, the "step of associating the calculated ratio with the presence or the absence of or severity of a disease caused by 22-23 turn Aβ in a subject" can be carried out by determining a subject with higher ratio of an amount of 22-23 turn Aβ relative to an amount of an antibody recognizing Aβ not having turn structure at amino acid positions 22 and or to an amount of Aβ, as a patient suffering from, or a patient with more severe form of a disease caused by 22-23 turn Aβ.

The method for diagnosing a disease caused by 22-23 turn Aβ etc. of the present invention may be implemented by combining with other index which has been already used as an index of Alzheimer's disease.

The sample derived from a patient used in the method of the present invention is not limited as long as expression of a biomarker can be detected and, for example, a tissue sample or a liquid collected from a subject as a sample can be used. A used sample is not limited as long as it can be a subject of measurement of the present invention, and includes a tissue, blood, plasma, serum, a lymph fluid, urine, a serous fluid, a spinal fluid (for example, a cerebrospinal fluid), a joint fluid, an aqueous humor, a lacrimal fluid, saliva or fractionated or treated substances thereof, and preferably is a brain tissue or blood (including plasma and serum). A sample derived from a patient used in the method of the present invention may be pre-treated prior to a measurement test, or a sample collected from the patient may be used as it is. Analysis according to the diagnosis method of the present invention can be qualitative, quantitative or semiquantitave. A disease caused by 22-23 turn Aβ in the diagnosis method of the present invention is preferably Alzheimer's disease. In the above description, the method for diagnosing a disease caused by 22-23 turn Aβ may be interchangeably read as a method for providing information for diagnosing a disease caused by 22-23 turn Aβ, or as a method for monitoring the state or progression of a disease caused by 22-23 turn Aβ.

In this specification, a phrase of "associating" used in the context of measured 22-23 turn Aβ and the presence or the absence of or severity of a disease caused by 22-23 turn Aβ in diagnosing a disease caused by 22-23 turn Aβ means comparison of presence, a level or an existence ratio of 22-23 turn Aβ in a subject, with presence, a level or an existence ratio of 22-23 turn Aβ in a patient of the disease caused by 22-23 turn Aβ or in a patient who is known to be probably the disease caused by 22-23 turn Aβ, or alternatively in a patient who was not a disease caused by 22-23 turn Aβ or in a patient who is believed not to be a disease caused by 22-23 turn Aβ. A level or a ratio of 22-23 turn Aβ in a patient to be a comparison subject can be known, for example, by the disclosure of the present invention, or by measuring a level of 22-23 turn Aβ in a sample derived from a patient who is known to have a disease caused by 22-23 turn Aβ or whom severity of the disease caused by 22-23 turn Aβ has been already found, or by assessment in combination with assessment with other index of a disease caused by 22-23 turn Aβ. Utilizing a level or a ratio of 22-23 turn Aβ, a possibility that a patient suffers from a disease caused by 22-23 turn Aβ, or a severity thereof can be determined. Association of a level or a ratio of 22-23 turn Aβ with a disease caused by 22-23 turn Aβ can be performed by statistical analysis. A statistical significance can be determined by comparing two or more populations, and determining a reliance interval and/or a p value (Dowdy and Wearden, Statistics for Research, John Wiley & Sons, New York, 1983). The reliance interval of the present invention may be, for example, 90%, 95%, 98%, 99%, 99.5%, 99.9% or 99.99%. The p value of the present invention may be, for example, 0.1, 0.05, 0.025. 0.02, 0.01, 0.005, 0.001, 0.0005. 0.0002 or 0.0001.

Preferably, 22-23 turn Aβ can be associated with a disease caused by 22-23 turn Aβ or severity thereof by its existence amount or existence ratio. For example, regarding a level of 22-23 turn Aβ, association may be performed by setting a threshold level as an index of suffering of a disease caused by 22-23 turn Aβ or by setting a threshold level for each severity as an index of severity of the disease, and then comparing a level of 22-23 turn Aβ in a sample derived from a patient with the threshold level. Such threshold level can be set, for example, so that sensitivity becomes 50, 55, 60, 65, 70, 75, 80, 85, 90, 91, 92, 93, 94, 95, 96, 97 or 98% or more. A threshold level can be set so that a specificity becomes 40, 45, 50, 55, 60, 65, 70, 75, 80, 85, 90, 91, 92, 93, 94, 95, 96, 97, or 98% or more. Alternatively, regarding a ratio of 22-23 turn Aβ, and other Aβ (for example, Aβ not having turn structure at amino acid positions 22 and 23 or entire Aβ), association may be performed by setting a threshold level as an index of suffering of a disease caused by 22-23 turn Aβ or by setting a threshold level for each severity as an index of severity of the disease, and comparing a ratio of 22-23 turn Aβ relative to other Aβ in a sample derived from a patient with the threshold level. Such threshold level can be set, for example, so that sensitivity becomes 50, 55, 60, 65, 70, 75, 80, 85, 90, 91, 92, 93, 94, 95, 96, 97 or 98% or more. A threshold level can be set so that a specificity becomes 40, 45, 50, 55, 60, 65, 70, 75, 80, 85, 90, 91, 92, 93, 94, 95, 96, 97 or 98% or more.

In order to describe the present invention in more detail, Examples will be shown below, but the present invention is not limited thereto. In addition, all references cited throughout the present application are incorporated into the present application by reference. All text of Japanese Patent Application 2009-239542 on which the present application claims the priority is incorporated entirely into the present application.

EXAMPLE 1

Preparation of Antibody to Toxic Conformer Having Turn Structure at Amino Acid Positions 22 and 23 of Aβ42, and Enzyme Immunoassay In an experiment of Example 1, maintenance and experiments of a mouse were performed according to a protocol approved by Animal Protection Committee Immuno-Biological Laboratories Co., Ltd. A molecular weight of G9C, E22P-Aρ9-35 and E22P-Aβ9-35 was confirmed using MALDI-TOF-MS (K. Irie et al. (1998), J. Am. Chem. Soc., 120:9159-9167).

(1) Obtaining of an Antibody Binding to Toxic Conformer of Aβ42

According to the reported method (K. Murakami et al. (2002), Biochem. Biophys. Res. Commun., 294:5-10; K. Murakami et al. (2007), ChemBioChem, 8:2308-2314), G9C, E22P-Aβ9-35 peptide (CYEVHHQKLVFFAPDVGSNK-GAIIGLM: SEQ ID: No. 1) was synthesized, and used as an immunogen. In the N-terminal, cysteine was added in place of glycine at position 9, and bound to a carrier protein bovine thyroglobulin (Y. Horikoshi et al. (2004), Biochem. Biophys. Res. Commun., 319: 733-737). A BALB/c mouse (Charles River Laboratories Japan Inc., Japan) was immunized with 50 mg/mouse of G9C, E22P Aβ9-35 peptide fusion once a week for one month. The resulting clone was cultured in a 96-well Maxisorp plate (Nunc, Denmark) coated with 50 mg/mL of various antibody mutants at room temperature for 1 hour, treated with a horseradish peroxidase-bound anti-mouse IgG antibody (Sigma, St. Louis, Mo., USA), and quantitated with 3,3',5,5'-tetramethylbenzidine (Pierce, Rock Field, Ill., USA) or an o-phenylenediamine dihydrochloride substrate (Sigma). Among the resulting 45 clones, clones having higher ability to bind to Aβ mutants which are more likely to take a β-turn structure at positions 22 and 23 (E22Q-Aβ42, E22G-Aβ42, E22K-Aβ42, E22P-Aβ42, and D23N-Aβ42) (K. Murakami et al. (2003), J. Biol. Chem., 278:46179-46187) (FIG. 1) were screened, and selected 7 clones were subcloned. Screening was repeated to remove clones which were low positive or false positive. The obtained 7 clones were further screened by Western blot to obtain a clone IBL-101 (not shown). This hybridoma was deposited at National Institute of Advanced Industrial Science and Technology, Incorporated Administrative Agency, International Patent Organism Depository (Tsukuba Center Central 6, 1-1-1 Higashi, Tsukuba-shi, Ibaraki, Japan). Date of deposit is Oct. 14, 2009, registration number is FERM BP-11290.

(2) Measurement of the Ability of Clone IBL-101 to Bind to E22P-Aβ42, Aβ42, Aβ40, and E22V-Aβ42

The ability of the resulting monoclonal antibody IBL-101 to bind to E22P-Aβ42, Aβ42, Aβ40, and E22V-Aβ42 was measured by an enzyme immunoassay. It has been reported that E22V-Aβ42 hardly takes a turn structure because of introduction of valine into position 22 (P. Y. Chou et al. (1977), J. Mol. Biol., 115:135-175). As a control antibody, a monoclonal antibody 4G8 having an epitope at 18 to 22 residues of an Aβ sequence (which are not included in turn structure part) (H. M. Wisniewski et al. (1989), Acta. Neuropathol., 78:22-27) was used. E22P-Aβ42, Aβ42, Aβ40, E22V-Aβ42, or as a control, 0.1% (w/v) BSA was added to a 96-well plate coated with 0.125 mg/mL, 0.25 mg/mL, 0.5 mg/mL, or 1.0 mg/mL of each antibody (IBL-101 or 4G8).

(3) Measurement of the Ability of Clone IBL-101 to Bind to 22K-23E, and P3-Aβ42

Figure 2:
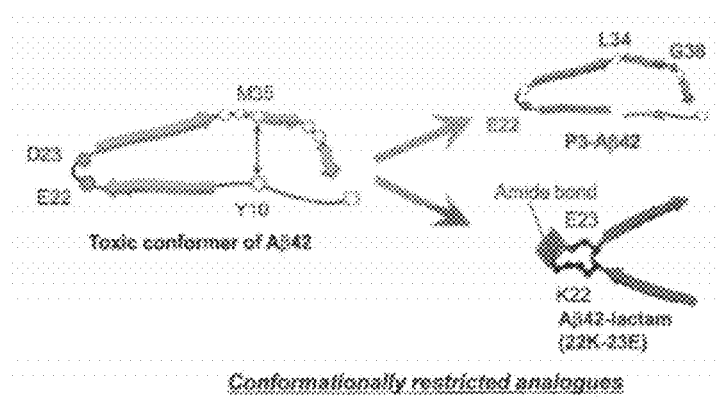
FIG. 2 is a view showing a structure of a conformation-fixed analogue Aβ-lactum (K-22-E23) of Aβ42 having a turn at positions 22 and 23, and a substitution site of a triple Aβ mutant (P3-Aβ42) in which three sites which can take turn structures are substituted with a proline residue.

As in Example 1 (2), the ability of monoclonal antibody IBL-101 to bind to a configuration-fixed analogue of Aβ42 Aβ-lactum (22K-23E) (Y. Masuda et al. (2009), ChemBioChem., 10:287-295) having a turn at positions 22 and 23 due to covalent bond of side chains of amino acids at positions 22 and 23, and to a triple Aβ mutant in which three sites which can take turn structures are substituted with a proline residue (P3-Aβ42) (A. Morimoto et al. (2004), J. Biol. Chem., 279: 52781-52788) (FIG. 2) was measured.

(4) Results

Figure 3:
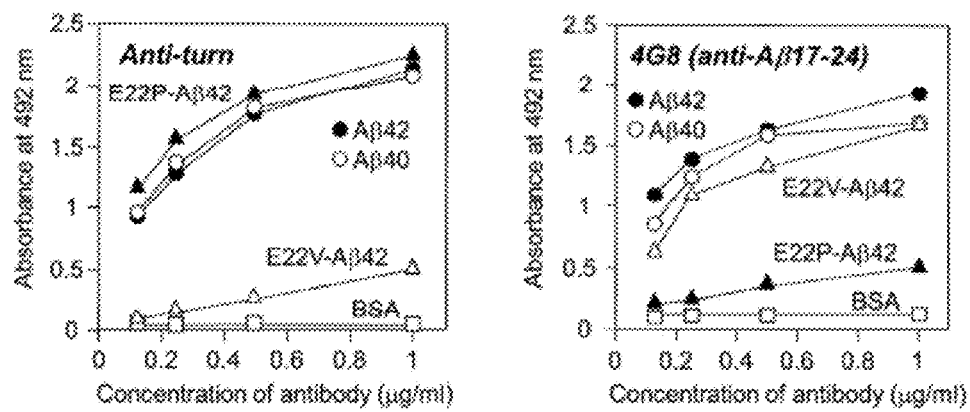
FIG. 3 is a graph showing the results of ELISA assay measuring binding of a monoclonal antibody IBL-101 or a monoclonal antibody 4G8 to Aβ42. A left graph shows results of IBL-101, and a right graph shows results of 4G8. In the graph, a vertical axis represents absorbance at OD492, and a horizontal axis represents a concentration of immobilized each monoclonal antibody. In the graph, a black circle indicates Aβ42, a white circle indicates Aβ40, a black triangle indicates E22P-Aβ42, a white triangle indicates E22V-Aβ42, and a white square indicates 0.1% (v/w) BSA.

Results of measurement of the ability to bind to E22P-Aβ42, Aβ42, Aβ40, and E22V-Aβ42 are shown in FIG. 3. IBL-101 exhibited strong immune reactivity to E22P-Aβ42, Aβ42 and Aβ40, but exhibited low affinity to E22V-Aβ42. On the other hand, the control antibody 4G8 weakly reacted with E22P-Aβ42, and bound to E22V-Aβ42 equally to Aβ42 and Aβ40. Since E22V-Aβ42 hardly takes a turn structure at positions 22 and 23 (K. Murakami et al. (2003), J. Biol. Chem., 278:46179-46187), these results suggest that IBL-101 specifically recognizes Aβ42 having a turn structure, and 4G8 cannot recognize Aβ42 having a turn structure at positions 22 and 23. The binding ability of IBL-101 to Aβ42 as well as E22P-Aβ42 means that IBL-101 is not specific for the proline residue at position 22, although the immunogen has a substitution mutation at position 22 with proline which constitutes a turn structure being recognized by the antibody.

From the above, since IBL-101 is turn structure-specific, binding of IBL-101 to Aβ42 and Aβ40 indicates an existence of Aβ42 and Aβ40 having a turn structure at positions 22 and 23 in Aβ42 and Aβ40.

Figure 4:
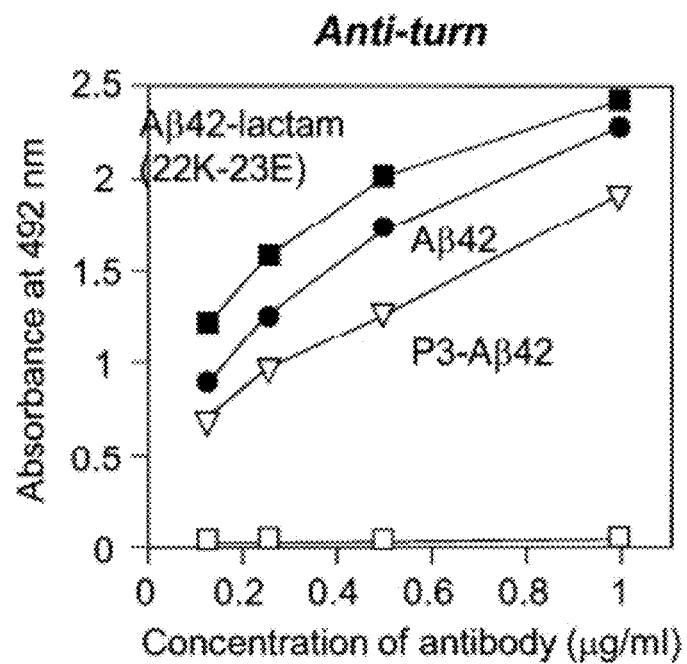
FIG. 4 is a graph showing the results of ELISA assay measuring binding of a monoclonal antibody IBL-101 to Aβ42, Aβ-lactum (22K-23E), and P3-Aβ42. In the graph, a vertical axis indicates absorbance at OD492, and a horizontal axis indicates a concentration of immobilized IBL-101. In the graph, a black circle indicates Aβ42, a black square indicates Aβ-lactum (22K-23E), and a white reverse triangle indicates P3-Aβ42.

The results of measurement of the ability to bind to 22K-23E, and P3-Aβ42 are shown in FIG. 4. IBL-101 also showed dose-dependent binding to these mutants, as shown to Aβ42. Therefore, these results also support that IBL-101 specifically recognizes a turn structure of Aβ42.

EXAMPLE 2

Effect of Monoclonal Antibody IBL-101 on Aβ42-Induced Neural Cell Toxicity

In order to determine whether or not the monoclonal antibody IBL-101 can inhibit cytotoxicity of Aβ42, Aβ42-induced neural cell toxicity in PC12 cells was assessed by an MTT assay (K. Murakami et al. (2003), J. Biol. Chem., 278: 46179-46187). One μM of Aβ42 or E22P-Aβ42 was added to cells alone, or together with 0.36 μM of a monoclonal antibody IBL-101, and the cells were cultured at 37° C. for 48 hours. A concentration of Aβ used was set to be $10^{-6}$ M near an IC50 value of wild-type Aβ42.

Figure 5:
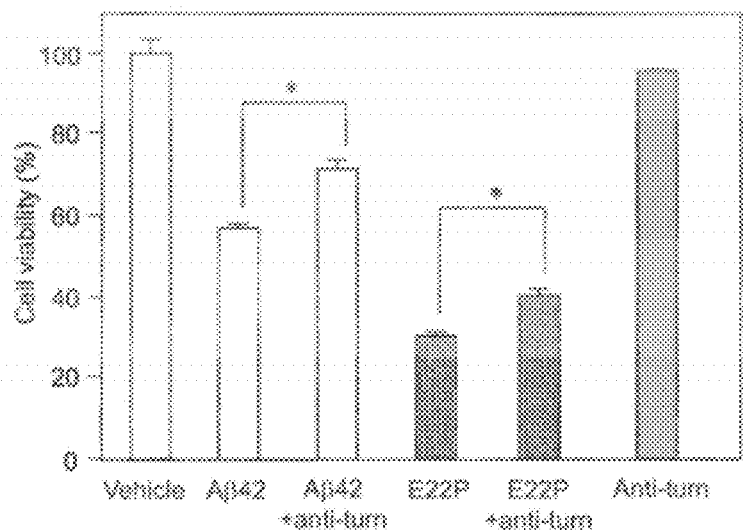
FIG. 5 is a graph showing neural cytotoxicity of Aβ42 and E22P-Aβ42 on PC12 cells, and the inhibitory effect of IBL-101 on the neural toxicity. In the graph, a vertical axis indicates a cell viability (%). An asterisk indicates $p<0.05$.

Results are shown in FIG. 5. PC12 cells treated with 1 μM of Aβ42 showed lower survival ability as compared with the control cell. By adding 0.36 μM of a monoclonal antibody IBL-101, cytotoxicity of Aβ42 was inhibited. Neural toxicity resulted from E22P-Aβ42 which is more likely to form a toxic conformer of Aβ42 than wild-type Aβ42 was similarly inhibited by IBL-101. Therefore, it was shown that the monoclonal antibody IBL-101 inhibits cytotoxicity resulted from Aβ42 and a toxic conformer of Aβ42.

EXAMPLE 3

Immunohistochemical Staining of Human AD Patient Brain and Brain of APP Transgenic Mouse (1) Preparation of Human Brain Under informed consent obtained from a written paper from a family of a patient, a hippocampal region tissue slice and a frontal lobe region tissue slice of brains from seven AD patients, six non-disease control individuals, and two other disease patients (case 14: circulatory disease; case 15: post-polio syndrome) were used in this experiment. The consent and an autopsy were approved by an ethic committee of Tokyo Metropolitan Instituted of Gerontology and Tokyo Metropolitan Geriatric Medical Center Hospital. Results of neuropathological diagnosis of each individual are shown in the following Table 1. Definite diagnosis of AD in the present experiment was made from neurofibrillary tangle and the presence of a senile plaque in hippocampus and a neocortex.

(2) Preparation of Transgenic Mouse Brain

Brains obtained from two types of APP transgenic mice, Tg2576 (K. Hsiao et al. (1996), Science, 274:99-102) and J20 (L. Mucke et al. (2000), J. Neurosci., 20:4050-4058) were dissected, fixed in 4% paraformaldehyde (Wako Pure Chemical Industries. Co., Ltd., Osaka, Japan) for 3 to 5 days, embedded in a paraffin, and cut into a 5 μM thickness on a microtome according to the conventional method. The mice used in the present experiment were maintained and subjected to an experiment, according to a protocol approved by Animal Committee of Tokyo Metropolitan Instituted of Gerontology.

The paraffin was removed from the slice, and the slice was hydrated, washed with a phosphate-buffered physiological saline (PBS), and treated with formic acid for a short time. In order to prevent endogenous peroxidation, after incubating in 3% hydrogen peroxide-containing methanol, the slice was blocked with 10% normal goat serum-containing PBS, and incubated with a primary antibody IBL-101 (1:540) or 4G8 (1:1000) (Signet Laboratories Inc., Dedham, Mass., USA) at 4° C. overnight. Thereafter, a biotinated secondary antibody (Vector Laboratories, Burlingame, Calif., USA) was added and incubated at room temperature for 30 minutes. Immunological reactivity was visualized using an ABC elite kit (Vector Laboratories) according to a protocol of a manufacturer.

3,3'-Diaminobenzidine (Sigma) was used as a chromogen. The slice was comparison-stained with hematoxylin.

(3) Inhibition Assay

An IBL-101 monoclonal antibody was pre-treated by contacting with 200-fold or more of an immunogen (G9C, E22P-Aβ9-35 peptide) in mole number, and used for staining a brain of an AD patient (case 5).

(4) Results

Figure 6:
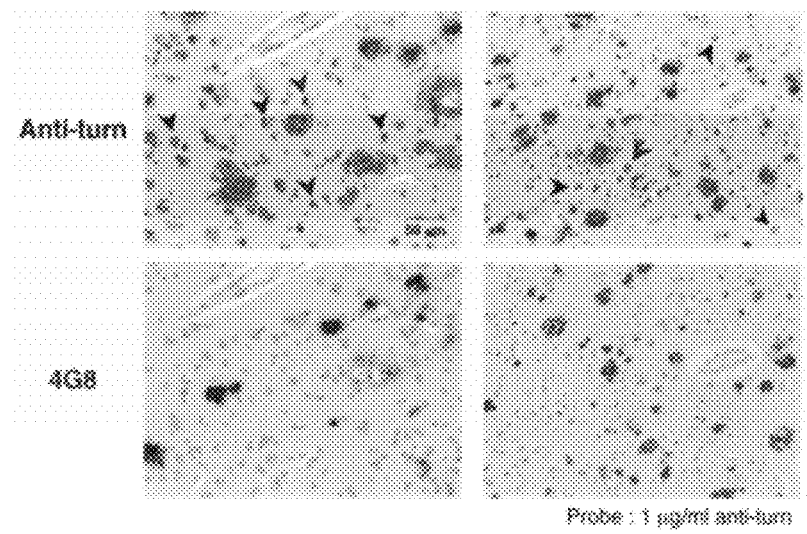
FIG. 6 shows photographs of hippocampal tissue slice of AD patients (case 1 and case 2), stained with IBL-101 monoclonal antibody or 4G8 monoclonal antibody. In the photographs, arrow head symbols indicate a site where intracellular region was stained. A scale bar indicates 50 μm.
Figure 7:
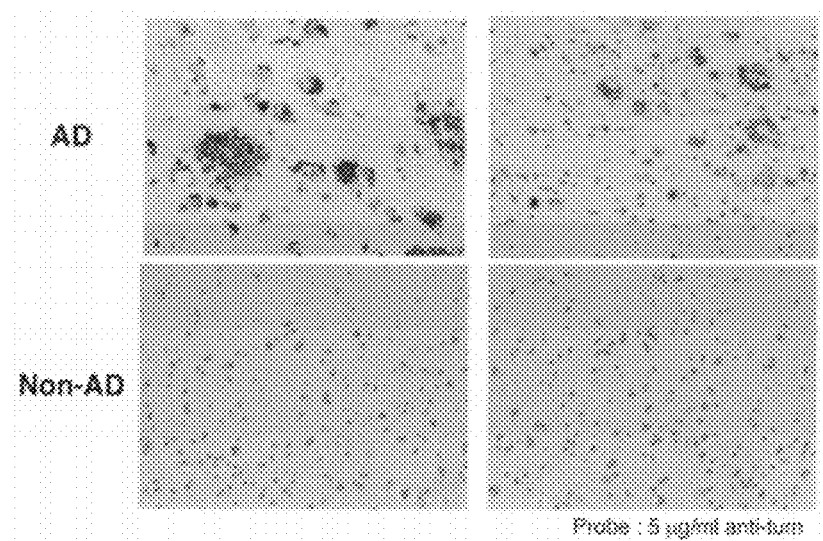
FIG. 7 shows photographs of frontal lobe tissue slice of AD patients (case 1 and case 2) and non-AD patients (case 3 and case 4), stained with IBL-101 monoclonal antibody.

Results of staining of a hippocampal region tissue slice of an AD patient (case 1 and case 2) with an IBL-101 monoclonal antibody or a 4G8 monoclonal antibody are shown in FIG. 6, and results of staining of a frontal lobe region tissue slice of an AD patient (case 1 and case 2) and a non-AD patient (case 3 and case 4) with an IBL-101 monoclonal antibody are shown in FIG. 7. As shown in FIG. 6, both antibodies reacted with a typical amyloid plaque, while some intracellular stainings were recognized (arrow head symbol) only when the IBL-101 monoclonal antibody was used. As shown in FIG. 7, this staining with the IBL-101 monoclonal antibody was recognized little in a brain of a non-AD patient.

Results of staining with the IBL-101 monoclonal antibody for all experimented cases are shown in the following Table 1. "SP" in a column of "IBL-101", "SP" indicates staining of a senile plaque, and "IA" indicates staining of intracellular amyloid. As a result of examination of reactivity of IBL-101 with intracellular amyloid, intermediate or more staining was observed in 6 of 7 AD patients, and mild or little staining was observed in a control individual. This shows that intracellular amyloid (particularly, Aβ having a turn structure at positions 22 and 23 of Aβ42) is involved in the onset of AD. Since accumulation of intracellular Aβ precedes aggregation of extracellular Aβ (Y. Ohyagi et al. (2008), Curr. Alzheimer Res. 5: 555-561), results of the present experiment showed that accumulation of intracellular Aβ can be utilized in diagnosis and assessment of AD.

TABLE 1

| | | | | | IBL-101 | | |
|---|---|---|---|---|---|---|---|
| case | age | sex | CDR | Braak | SP | IA | NP diagnosis |
| 1 | 96 | M | 3 | 6 | +++ | ++ | AD |
| 2 | 83 | F | 3 | 5 | +++ | +++ | AD |
| 3 | 84 | M | 3 | 5 | ++ | ++ | AD |
| 4 | 86 | F | 1 | 5 | +++ | ++ | AD |
| 5 | 91 | F | 1 | 5 | ++ | +++ | AD |
| 6 | 82 | F | 3 | 5 | +++ | +++ | AD |
| 7 | 86 | F | 3 | 6 | ++ | ++ | AD |
| 8 | 84 | M | 2 | 6 | +++ | ++ | AD |
| 9 | 76 | M | 3 | 6 | ++ | ++ | AD |
| 10 | 84 | F | 3 | 5 | ++ | + | AD |
| 11 | 84 | F | 2 | 4.5 | ++ | ++ | AD |
| 12 | 86 | F | 3 | 5 | ++ | ++ | AD |
| 13 | 87 | F | 3 | 5 | ++ | +++ | AD |
| 14 | 74 | M | 0 | 5 | +++ | ++ | AD |
| 15 | 82 | F | 1 | 5 | ++ | + | AD |
| 16 | 81 | M | 2 | 6 | ++ | + | AD |
| 17 | 87 | M | 3 | 6 | +++ | ++ | AD |
| 18 | 79 | M | 0.5 | 2 | — | + | non-AD |
| 19 | 80 | F | 0 | 2 | — | ++ | non-AD |
| 20 | 82 | F | N/A | 2 | — | + | non-AD |
| 21 | 80 | M | 0 | 2 | + | + | non-AD |
| 22 | 75 | M | 0 | 1 | — | + | non-AD |
| 23 | 69 | M | N/A | 1 | — | — | non-AD |
| 24 | 70 | M | 0 | 1 | — | + | non-AD |
| 25 | 68 | M | 0 | 1 | — | + | non-AD |
| 26 | 67 | M | N/A | 1 | + | + | non-AD |
| 27 | 67 | M | 0 | 2 | + | — | non-AD |
| 28 | 80 | M | 0.5 | 2 | + | — | non-AD |
| 29 | 72 | M | 0 | 1 | + | + | non-AD |
| 30 | 81 | M | 0 | 1 | — | + | non-AD |
| 31 | 82 | M | 0 | 1 | — | — | non-AD |
| 32 | 78 | F | N/A | 1 | — | — | non-AD |
| 33 | 83 | M | N/A | 1 | — | — | non-AD |
| 34 | 77 | F | 0 | 1 | — | + | non-AD |
| 35 | 79 | F | N/A | 1 | — | ++ | non-AD |

[a]CDR, clinical dementia rating; Braak, Braak staging; SP, senile plaque; IA, intracellular amyloid; NP diagnosis, neuropathological diagnosis; AD, Alzheimer's disease. +, mild reactivity; ++, moderate reactivity; +++, strong reactivity; —, not detected; N/A, not available.

Figure 8:
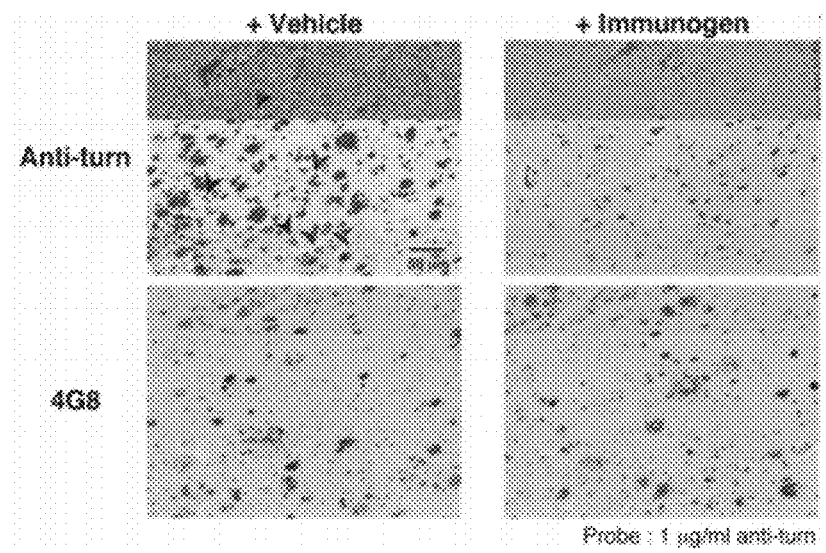
FIG. 8 shows photographs of brain tissue stained after pre-treatment with an immunogen (inhibitory assay). In the photographs, arrow head symbols indicate a site where intracellular region was stained. A scale bar indicates 50 μm. "+Vehicle" indicates an antibody pre-treated with a solution not containing immunogen (control), and "+Immunogen" indicates an antibody pre-treated with immunogen.

The results of an inhibition assay are shown in FIG. 8. Pre-treatment with an immunogen resulted in no stain of an AD patient brain slice. In a control experiment, 4G8 did not react with an immunogen of IBL-101 at all. From these results, it was shown that IBL-101 specifically recognizes Aβ, particularly Aβ having a turn structure at positions 22 and 23 in a cell and at a senile plaque.

Figure 9:
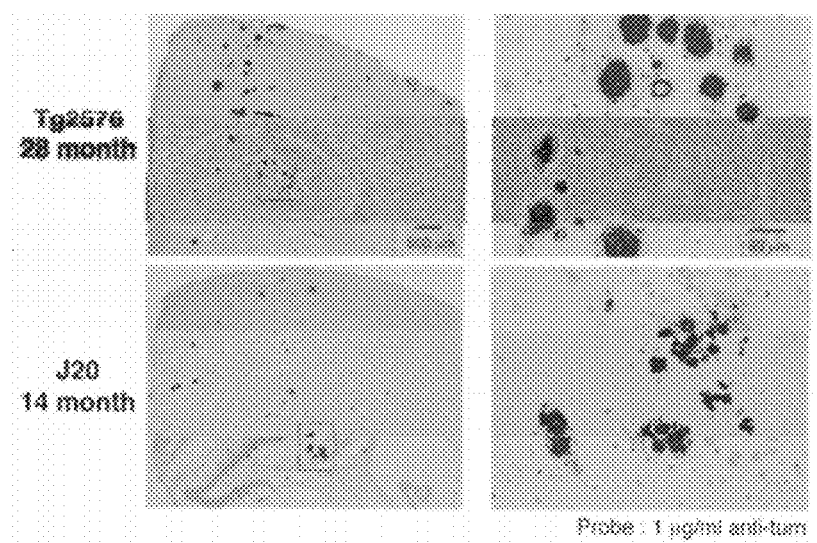
FIG. 9 shows photographs of brains of two types of transgenic mice (Tg2576 and J20) stained with IBL-101 monoclonal antibody. Right photographs are an enlarged photograph of left photographs surrounded with a square. In left photographs, a scale bar indicates 500 μm and, in a right photograph, a scale bar indicates 50 μm.

Results of staining of brains of two types of transgenic mice with the IBL-101 monoclonal antibody are shown in FIG. 9. In brains of transgenic mice, intracellular staining with IBL-101 did not be observed.

EXAMPLE 4

Western Blotting

In order to confirm whether or not an IBL-101 antibody recognizes an oligomer of Aβ in a human brain, Western blotting was carried out.

(1) Preparation of Tissue

A frontal lobe tissue was added to a 10-fold amount (w/v) of 50 mM of Tris-HCl buffer (pH 7.6) (TBS) containing 150 mM NaCl, a protease inhibitor mixed solution (Complete EDTA-free, Roche Diagnostics, Indianapolis, Ind., USA), and a phosphatase inhibitor mixed solution (Phos STOP, Roche Diagnostics), to which 0.7 μg/mL of pepstatin A (Peptide Institute Inc., Osaka, Japan) and 1 mM of phenylmethylsulfonyl fluoride (Sigma) had been added, and homogenized. The homogenate was centrifuged at 186,000 g for 30 minutes at 4° C. using Optima TL ultracentrifuge and TLA100.4 rotor (Beckman, Palo Alto, Calif., USA), and the supernatant and pellets were collected. The obtained supernatant was used as a soluble fraction (soluble fr.). The pellets were dissolved by ultrasound treatment in protease inhibitor-containing 70% formic acid (Saido, T. C. et al., (1995), Neuron 14, 457-466). The solubilized pellets were centrifuged at 186,000 g for 30 minutes at 4° C., and the resulting supernatant was neutralized with 1M of a Tris base (pH 11) at an amount of 1:20 (v/v), and used as an insoluble fraction (Insoluble fr.). In order to assess cross reactivity of an IBL-101 antibody with APP, recombinant human APP (R & D, Minneapolis, Minn., USA) including a protease Nexin II was used.

(2) Western Blotting

Two μg/μL of each of the soluble fraction, the insoluble fraction, and recombinant APP were subjected to Western blotting using 10 to 20% Tricine Gel (Invitrogen, Gaithersburg, Md., USA), and transferred onto a PVDF membrane (pore size 0.2 μm) (Biorad, Hercules, Calif., USA). The membrane was heated in PBS for 1 minute using a microwave oven, blocked with TBS-T (0.01% Tween-20, and 2.5% skim milk-containing TBS), and reacted with a primary antibody (IBL-101: 5 μg/mL, 4G8: 1 μfuram/mL, 82E1: 1 μg/mL, anti-APP-N-terminal antibody and anti-APP-C-terminal antibody: 1 μg/mL each, anti-actin antibody (Sigma): 1

µg/mL, anti-lamin antibody (ImQuest): 1 µg) at 4° C. overnight. In an experiment for confirming antigenicity, a primary antibody (IBL-101) was pre-treated with a 200-fold mole excessive antigen (G9C, E22P-Aβ9-35 peptide) in advance. Thereafter, the membrane was washed with TBS-T, and reacted with a secondary antibody at room temperature for 1 hour. Development was performed using an enhanced chemiluminescence ECL reagent (GE Healthcare, Buckinghamshire, UK), and luminescence intensity was quantified by using LAS-3000 (Fujifilm Corporation, Tokyo, Japan). In order to confirm the presence of a protein, Coomassie Brilliant Blue was used.

(3) Results

Figure 10:
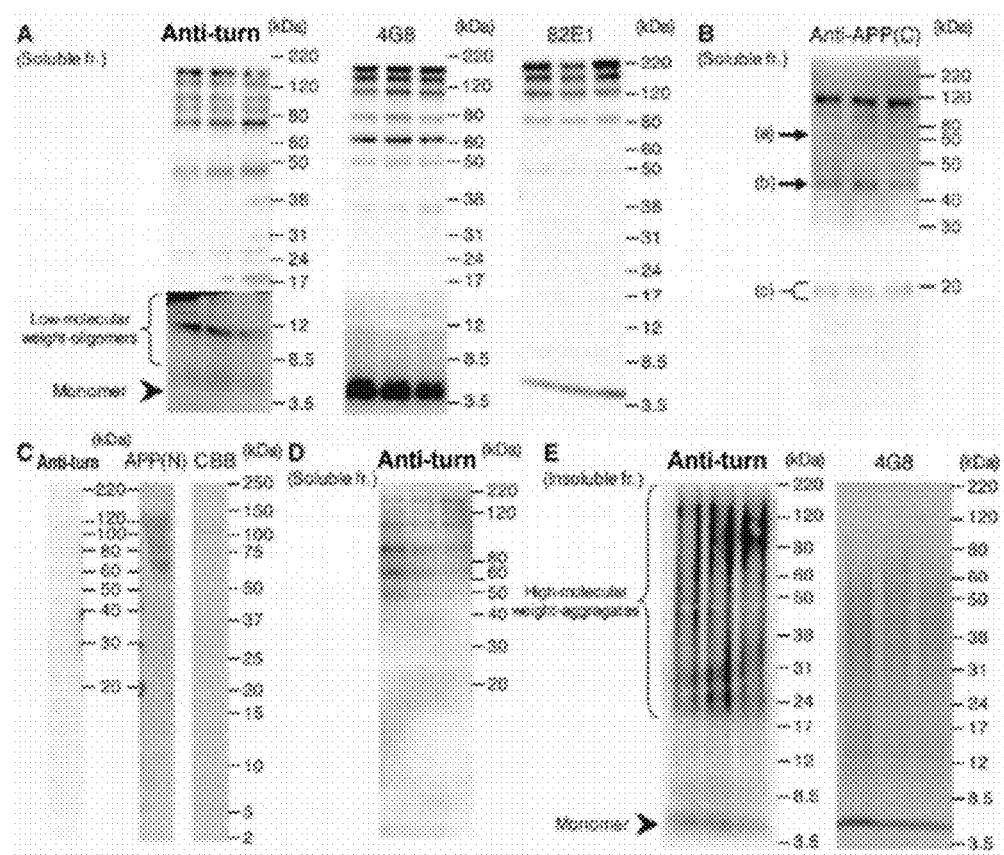
FIGS. 10A, 10B and 10D are photographs representing results of Western blotting of a 50 mM Tris-HCl buffer (pH7.6) (TBS) soluble fraction (Soluble fr.) of a brain from an AD patient with an IBL-101 monoclonal antibody (Anti-turn), 4G8 monoclonal antibody (4G8), 82E1 monoclonal antibody (82E1), and anti-APP-C-terminal antibody (Anti-APP(C)).
FIG. 10C is photographs showing the results of Western blotting of recombinant human APP with IBL-101 monoclonal antibody (Anti-turn), and anti-APP-N-terminal antibody (APP(N)).
FIG. 10E is photographs showing the results of Western blotting of a TBS insoluble fraction (Insoluble fr.) of a brain from an AD patient with IBL-101 monoclonal antibody (Anti-turn), and 4G8 monoclonal antibody (4G8).

Results are shown in FIG. 10. FIG. 10A shows results of Western blotting with IBL-101 antibody, 4G8 antibody, and 82E1 antibody for a soluble fraction prepared from a brain of an AD patient. FIG. 10B shows results of Western blotting with anti-APP-C-terminal antibody, anti-actin antibody, and anti-lamin antibody for a soluble fraction prepared from a brain of an AD patient. The anti-actin antibody and the anti-lamin antibody were used as an internal control. In the figures, (a) indicates lamin (70 kDa), (b) indicates β-actin (42 kDa), and (c) indicates a C-terminal fragment of APP.

The same pattern of staining for 82E1 antibody which does not bind to APP but binds only to Aβ (See International Publication WO 2005/080435, FIG. 4 and Horikoshi, Y. et al., (2004), Biochem. Biophys. Res. Commun. 319, 733-737) and 4G8 antibody indicated that the stained protein is Aβ. From the results of Example 1, it is considered that the protein stained with Anti-turn (IBL-101) is Aβ having a turn structure at positions 22 and 23 of Aβ42, and the protein stained with 4G8 is Aβ not having a turn structure. The results support that many Aβs having a turn structure are present in an AD patient. From a result of using IBL-101 antibody (FIG. 10A Anti-turn), it was shown that the antibody recognizes an oligomer of Aβ (Low-molecular weight-oligomers) (particularly, a trimer) which was observed as a band at around 12 to 17 kDa. This band was not observed in detection with 4G8 antibody or 82E1 antibody recognizing epitope located on N-terminal of Aβ (Horikoshi, Y. et al., (2004) Biochem. Biophys. Res. Commun. 319, 733-737) (FIG. 10A 4G8 and 82E1). The 4G8 antibody and the 82E1 antibody strongly reacted with a monomer of Aβ (shown by an arrow symbol in FIG. 10A). This result was consistent with that an oligomer of Aβ is easily formed by forming a turn structure.

Further, in a high molecular weight region, the IBL-101 antibody showed unique band pattern which was apparently different from the 4G8 antibody and the 82E1 antibody (FIG. 10A). A band pattern of the anti-APP-C-terminal antibody was also different from that of the IBL-101 antibody (FIG. 10B). The anti-APP-C-terminal antibody reacts with three isoforms of APP (APP695, APP751 and APP770), but does not react with secreted APPα and APPβ, α-cleaved and β-cleaved product of APP, respectively (Selkoe, D. J. (1994) Annu. Rev. Neurosci. 17, 489-517).

Results of reactivity experiment of the IBL-101 antibody with recombinant APP are shown in FIG. 10C. From this results, it was confirmed that the anti-APP-N-terminal antibody certainly reacted with APP, but the IBL-101 antibody did not react with recombinant APP. In the same experiment, existence of protein (APP) was also confirmed by Coomassie Brilliant Blue staining. From these results, it was confirmed that bands of high molecular weights detected with the IBL-101 antibody were derived from aggregates of Aβ, and were not APP.

In order to confirm antigenicity of the IBL-101 antibody, an adsorption experiment using an antigen was performed (FIG. 10D). As a result, as shown in FIG. 10D, bands of low molecular weight oligomer were observed little by pre-treatment with antigen. On the other hand, weak bands were observed at higher molecular weight. These results suggest that the IBL-101 antibody has more preferable immune reactivity on oligomers of low molecular weight.

FIG. 10E shows results of Western blotting with IBL-101 antibody and 4G8 antibody for an insoluble fraction prepared from a brain of an AD patient. The IBL-101 antibody reacted with high-molecular aggregates exhibiting a variety of molecular weights as well as a monomer (shown by an arrow symbol in FIG. 10E). On the other hand, a monomer was detected more clearly as compared with high-molecular weight aggregates by using the 4G8 antibody. Since a monomer of Aβ is highly degenerated by formic acid, the result of the present experiment indicates that the IBL-101 antibody is specific for a structure of not degenerated Aβ, particularly for a structure of Aβ present in an aggregate.

From the above results, it was shown that the IBL-101 antibody specifically recognizes a structure of Aβ characteristic in an aggregate, and particularly, specifically recognizes a turn structure in amino acid positions 22 and 23 of Aβ.

It was observed that an amount of oligomers of Aβ detected with IBL-101 was larger than that detected with 4G8. This indicates that in a brain of an AD patient, not only an amount of Aβ having a turn structure at positions 22 and 23 of Aβ42 is increased, but also a ratio of an amount of Aβ having the turn structure to an amount of Aβ having no turn structure is increased. Therefore, it was shown that diagnosis of AD can be also performed, by measuring a ratio of an amount of Aβ not having a turn structure and an amount of Aβ having the turn structure.

The invention claimed is:

1. An isolated antibody or an immunoreactive fragment thereof comprising the CDR1, CDR2 and CDR3 of the H-chain and the CDR1, CDR2 and CDR3 of the L-chain of the antibody produced by the hybridoma deposited as registration No. FERM-11290.

2. The antibody or fragment of claim 1 wherein one or more amino acids are substituted, deleted, modified, added and/or inserted and retains the antigen-binding specificity of the antibody produced by the hybridoma deposited as registration No. FERM-11290.

3. The antibody of or fragment claim 1 wherein the antibody or fragment is identical to that produced by hybridoma deposited as registration No. FERM-11290.

4. A kit for measuring amyloid β having a turn structure at amino acid positions 22 and 23, comprising an antibody or fragment of claim 1 and reagents for detecting binding of said antibody to said amyloid β.

5. The antibody or fragment of claim 1 that has VH and VL of the antibody produced by the hybridoma deposited as registration No. FERM-11290.

6. The antibody or fragment of claim 5 which further comprises the constant regions of a human antibody.

7. A pharmaceutical composition comprising an antibody of claim 1 as an active ingredient.

8. A method to treat Alzheimer's disease which comprises administering to a subject in need of said treatment an effective amount of the pharmaceutical composition of claim 7.

9. A method for measuring the level of amyloid β having a turn structure at amino acid positions 22 and 23 in a sample, comprising contacting the sample with an antibody or fragment of claim 1, and measuring any complex formed with said antibody or fragment.

10. A method for providing information for diagnosis of Alzheimer's disease in a test subject comprising steps of:
    contacting a sample derived from the test subject with at least one antibody or fragment of claim 1, and
    measuring binding of the antibody or fragment to any amyloid 0 having a turn structure at amino acid positions 22 and 23,
    determining a level of amyloid β having a turn structure at amino acid positions 22 and 23, whereby the level of amyloid β having a turn structure at amino acid positions 22 and 23 determines presence or absence or severity of Alzheimer's disease in the subject.

11. A method for measuring a ratio of amyloid β having a turn structure at amino acid positions 22 and 23 relative to total amyloid β in a sample, comprising:
    measuring a level of total amyloid β in the sample,
    contacting the sample with at least one antibody or fragment of claim 1 and measuring any level of amyloid β having a turn structure at amino acid positions 22 and 23, and
    calculating the ratio of the measured level of amyloid β having a turn structure at amino acid positions 22 and 23 to the measured level of total amyloid β.

12. A method for providing information for diagnosis of Alzheimer's disease in a subject, comprising:
    measuring a level of total amyloid β in a sample derived from the test subject,
    contacting the sample with at least one antibody or fragment of claim 1 and measuring a level of amyloid β having a turn structure at amino acid positions 22 and 23,
    calculating the ratio of the measured level of amyloid β having a turn structure at amino acid positions 22 and 23 relative to the measured level of total amyloid β,
    whereby the ratio of the measured level of amyloid β having a turn structure at amino acid positions 22 and 23 relative to the measured level of total amyloid β determines presence or absence or severity of Alzheimer's disease in the subject.

* * * * *

UNITED STATES PATENT AND TRADEMARK OFFICE
CERTIFICATE OF CORRECTION

PATENT NO. : 8,710,193 B2  
APPLICATION NO. : 13/502347  
DATED : April 29, 2014  
INVENTOR(S) : Kazuhiro Irie et al.

Page 1 of 1

It is certified that error appears in the above-identified patent and that said Letters Patent is hereby corrected as shown below:

In the Claims:

At column 32, claim number 10, line number 10, please change "amyloid 0" to --amyloid β--

Signed and Sealed this  
Twenty-seventh Day of January, 2015

Michelle K. Lee  
*Deputy Director of the United States Patent and Trademark Office*